(12) United States Patent     (10) Patent No.:    US 8,563,258 B2
Sainte-Laudy et al.                    (45) Date of Patent:     Oct. 22, 2013

(54) ALLERGY TEST BASED ON FLOW CYTOMETRIC ANALYSIS

(75) Inventors: Jean Sainte-Laudy, Saint-Junien (FR); Michael Schneider, Therwil (CH); Jakob Matthias Weber, Reinach (CH)

(73) Assignee: Buhlmann Laboratories AG, Schonenbuch (CH)

( * ) Notice: Subject to any disclaimer, the term of this patent is extended or adjusted under 35 U.S.C. 154(b) by 241 days.

(21) Appl. No.: 12/677,402

(22) PCT Filed: Sep. 11, 2008

(86) PCT No.: PCT/EP2008/007494
§ 371 (c)(1),
(2), (4) Date: May 4, 2010

(87) PCT Pub. No.: WO2009/033691
PCT Pub. Date: Mar. 19, 2009

(65) Prior Publication Data
US 2010/0221756 A1    Sep. 2, 2010

(30) Foreign Application Priority Data
Sep. 11, 2007    (EP) ..................................... 07017775

(51) Int. Cl.
*G01N 33/53*     (2006.01)
(52) U.S. Cl.
USPC ........................... 435/7.24; 424/805; 424/810
(58) Field of Classification Search
None
See application file for complete search history.

(56) References Cited

U.S. PATENT DOCUMENTS 5,717,100 A * 2/1998 Selnick et al. ................. 546/194
6,531,494 B1 * 3/2003 Khanna et al. ................ 514/352

FOREIGN PATENT DOCUMENTS

WO    WO 2007/093517 A1    8/2007

OTHER PUBLICATIONS

Sainte-Laudy et al., Inflamm. Res. 2007, 56:291-296.*
International Search Report of PCT/EP2008/007494 (Nov. 14, 2008).
G. Monneret et al., "Monitoring of Basophil Activation Using CD63 and CCR3 in Allergy to Muscle Relaxant Drugs", Clinical Immunology, vol. 102, No. 2 (Feb. 2002) pp. 192-199.
R. Boumiza et al., "The Basophil Activation Test by Flow Cytometry : Recent Developments in Clinical Studies, Standardization and Emerging Perspectives", Clinical and Molecular Allergy, vol. 3, No. 9 (2005) pp. 1-8.
M. L. Sanz et al., "Flow Cytometric Basophil Activation Test : A Review", J. Invest. Allergol. Clin. Immunol., vol. 12, No. 3 (2002) pp. 143-154.

* cited by examiner

*Primary Examiner* — Michael Szperka
(74) *Attorney, Agent, or Firm* — Millen, White, Zelano & Branigan, P.C.

(57) ABSTRACT

The invention pertains to a method for the determination of basophil activation induced by a test substance by flow cytometric measurement of the changes of the mean or median fluorescence intensities (MFI) of the basophilic $F_c\epsilon RI$ receptor present on the cell surface of basophils (MFI-$F_c\epsilon RI$) and/or the IgE antibodies bound to the $F_c\epsilon RI$ receptor (MFI-IgE), and the CD63 antigen exposed on the cell surface of basophils after their activation (MFI-CD63), by means of a mixture of anti-CD63, anti-$F_c\epsilon RI$ or anti-IgE, and anti-CCR3 antibodies each labelled with a distinct fluorophore, of which at least one antibody acts as a basophil selection marker and at least two antibodies act as basophil activation markers, and bringing the mean fluorescence intensities of the activation markers in correlation to obtain an Activation Index. These methods combining the measurement of an early (such as IgE, $F_c\epsilon RI$ or CD203c) and a late basophil activation marker (such as CD63), respectively, provide a markedly improved clinical sensitivity in allergy diagnosis over existing methods which consider only one activation marker, such as CD203c or CD63, expressed in percentage of basophil activation. It is also an aspect of the present invention to provide an ex-vivo allergy provocation test comprising the above-mentioned flow cytometric measurement and analysis of the results as well as a test kit for carrying out the test in-vitro.

28 Claims, 20 Drawing Sheets

ALLERGY TEST BASED ON FLOW CYTOMETRIC ANALYSIS

BACKGROUND

The present invention is directed to a flow cytometric analysis of allergen induced basophil activation. The particular combinations of antibodies labelled with different fluorophores in combination with a new approach to obtain the mean or median fluorescence intensities (MFI) resulting in the provision of an Activation Index which allows for a better correlation of the individual patient results to their clinical history and, therefore, provides a markedly improved clinical sensitivity over existing methods by maintaining a high specificity. Thereby, a novel in vitro allergy test is provided.

Human basophils are one class of leukocytes circulating in the blood stream and belong to the granulocytes. Despite their low abundance in human blood (less than 2% of the leukocyte fraction), they play a central role in allergic hypersensitivity reactions by releasing potent inflammatory mediators. Moreover, basophils represent the major interleukin-4 secreting human cell. Interleukin-4 plays a key immunological role.

Immunoglobulin E (IgE) represents one of the classes of immunoglobulins. It is known to participate in allergic reactions. Circulating IgE molecules bind to the basophil membrane via the high affinity FcεRI receptor. An allergen, usually a protein of a molecular size of more than 5000 Da, is able to crosslink two neighboured IgE molecules bound on the basophils. By this crosslinking, a complex process is activated at the membrane level by an increase of membrane fluidity leading to IgE/FcεRI receptor clustering, degranulation of the cells and initiation of ionic fluxes into the basophilic cells which ultimately lead to the release of inflammatory mediators, such as histamine or sulfidoleukotrienes, as well as to the expression on, up-regulation at or migration of glycoproteins to the basophil membrane. Examples of such glycoproteins are CD45, CD63 or CD203c which are members of the so-called clustered differentiation (CD) antigens.

Apart from the IgE mediated allergic reactions which can be induced by protein allergens, bivalent molecules, monovalent allergens (true haptens) presented to basophils by a carrier macromolecule, anti-IgE antibodies, anti-FcεRI receptor antibodies, etc, so-called non-IgE mediated reactions do also exist or are related to allergens for which an IgE mechanism has not been clearly established. The non-IgE mediated reactions are usually induced by low molecular weight substances such as a whole series of drugs, some food additives, other chemicals or agents, fMLP, complement factor C5a, etc. Both IgE and non-IgE mediated reactions may lead to basophil activation. However, the rate of positive reactions is much lower in non-IgE mediated processes. Oppositely to IgE mediated basophil activation, the underlying pathophysiological mechanism for non-IgE mediated basophil activation and allergic reactions, respectively, is still not known to date.

Basophil activation was first studied by quantification of the amount of mediator release (histamine and leukotriene C4) or by staining with specific fluorescent dyes and subsequent microscopic counting of fluorescent basophils. Later, the availability of flow cytometers capable of analysing several thousand cells per second led to the development of several methods first based on basophil staining with alcian blue (T. Nakagawa, B. M. Stadler, A. L. de Weck: Flow-cytometric analysis of human basophil degranulation. I. Quantification of human basophils and their degranulation by flow-cytometry. Allergy 1981, 36, 39-47; T. Nakagawa, O. Moyseyenko, A. L. de Weck: Flow-cytometric analysis of human basophil degranulation. Ill. Degranulation induced by allergens and antibodies in hay fever and bee venom allergic patients. Int Arch Allergy Appl Immunol 1981, 64, 201-209) and later with the use of fluorescently labelled antibodies specifically reacting with various basophilic membrane markers (reviewed by F. Hennersdorf, S. Florian, A. Jakob, K. Baumgartner, K. Sonneck, A. Nordheim, T. Biedermann, P. Valent, H. J. Bühring: Identification of CD13, CD107a, and CD164 as novel basophil activation markers and dissection of two response patterns in time kinetics of IgE-dependent upregulation. Cell Res 2005, 15, 325-335).

Early studies have demonstrated that quantification of allergen induced basophil activation by flow cytometric measurements is possible (P. Gane, C. Pecquet, H. Crespeau, P. Lambin, F. Leynadier, P. Rouger: Flow cytometric monitoring of allergen induced basophil activation. Cytometry 1995, 19, 361-365). The measurements have been carried out with aero-allergens such as protein extracts from grass or tree pollens, cat dander and dust mites. Upon basophil activation the following changes were detected: (i) a decrease in the number of detectable basophils, (ii) a decrease in IgE mean fluorescence intensity (MFI), and (iii) an increase in CD45 MFI. The increase of the CD45 MFI was detected for all aero-allergens tested clearly indicating that expression of the CD45 molecule on basophils is increased. It was concluded that the increase in CD45 expression is a measure of basophil activation and can, therefore, facilitate investigations on allergen induced basophil activation.

Since it turned out that CD45 was not an optimal expression marker to follow basophil activation, the discovery of the basophil activation marker, CD63 (E. F. Knol, F. P. Mul, H. Jansen, J. Calafat, D. Roos: Monitoring human basophil activation via CD63 monoclonal antibody 435. J Allergy Clin Immunol 1991, 88, 328-338), and its first use for analysing allergen induced basophil activation as described by Sainte-Laudy et al. (J. Sainte-Laudy, C. Vallon, J.-C. Guérin: Analyse de l'expression membranaire du marqueur CD63 par activation du basophil humain. Applications au diagnostic allergologique. Allergie et Immunologie 1994, 26, 211-214; A. Funes, J. Sainte-Laudy, A. Sabbah: Methode pour l'analyse de l'activation des basophiles humain par mésure de l'expression membranaire du marqueur CD63. FR 2 765 341-A1) was considered a major breakthrough. Among many others, a study of flow cytometric analysis of insect venom allergy looking at CD63 expression on basophils has demonstrated a perfect correlation with the clinical history of the patients as well as a high correlation to leukotriene release which is a known indicator of basophil activation (J. Sainte-Laudy, A. Sabbah, M. Drouet, M. G. Lauret, M. Loiry: Diagnosis of venom allergy by flow cytometry. Correlation with clinical history, skin tests, specific IgE, histamine and leukotriene C4 release. Clin Exp Allergy 2000, 30, 1166-1171). The sensitivity and specificity (both 100%) of the flow cytometry method was better than that of skin tests and specific IgE determination. Hence, the use of flow cytometry based on percentage CD63 expression for the diagnosis of insect venom allergy has been strongly advocated and ever since, this method has been applied to a wide panel of protein and drug allergens (reviewed, by M. L. Sanz, J. P. Maselli, P. M. Gamboa, A. Oehling, I. Diéguez, A. L. de Weck: Flow cytometric basophil activation test: a review. J Investig Allergol Clin Immunol 2002, 12, 143-154; D. G. Ebo, J. Sainte-Laudy, C. H. Bridts, C. H. Mertens, M. M. Hagedorens, A. J. Schuerwegh, L. S. de Clerck, W. J. Stevens: Flow-assisted allergy diagnosis: current applications and future perspectives. Allergy 2006, 61, 1028-1039).

Later, protocols using the increase of CD203c expression as a basophil activation marker for allergy diagnosis have also been described as alternatives to the use of CD63 (eg. I. J. Platz, M. Binder, A. Marxer, G. Lischka, P. Valent, H. J. Bühring: Hymenoptera-venom-induced upregulation of the basophil activation marker ecto-nucleotide pyrophosphatase/phosphodieasterase 3 (CD203c) in sensitized individuals. Int Arch Allergy Immunol 2002, 126, 335-342; R. Boumiza, G. Monneret, M. F. Forissier, J. Savoye, M. C. Gutowski, W. S. Powell, J. Bienvenu: Marked improvement of the basophil activation test by detecting CD203c instead of CD63. Clin Exp Allergy 33, 259-265; A. Ocmant, Y. Peignois, S. Mulier, L. Hanssens, A. Michils, L. Schandene: Flow cytometry for basophil activation markers: the measurement of CD203c upregulation is as reliable as CD63 expression in the diagnosis of cat allergy. J Immunol Methods 2007, 320, 40-48).

Monneret et al (Monneret G et al: Monitoring of basophil activation using CD63 and CCR3 in allergy to muscle relexant drugs. Clin Immunol, 2002, 102 (2), 192-199) describe the monitoring of basophil activation using CD63 and/or CCR 3. Data were obtained from flow cytometry which were compared to skin tests, specific IgE and histamine release results. The flow cytometric protocol described by Monneret et al appears to be useful in allergy diagnosis, since it is specific and complementary to specific IgE detection.

Boumiza et al. (Boumiza R, Debard A-L, Monneret G: The basophil activation test by flow cytometry: recent developments in clinical studies, standardization and emerging perspectives. Clin Mol Allergy 2005, 3 (9), 1-8) disclose in a review article the recent developments in clinical studies, standardization and perspectives of the flow cytometric technique. The review is focused on flow cytometry as a tool for monitoring basophil activation upon allergen challenge by detecting surface expression of degranulation/activation markers like CD63 or CD203c. Boumiza et al. focus on the use of anti-CD45 antibodies in the presence of CRTH2/DP2 or IgE for basophil recognition together with a specific staining protocol so that the basophil activation test is useful as a tool for in vitro diagnosis of immediate allergy.

Summing up, it has been demonstrated that flow cytometric analysis of basophil activation provides both high sensitivities and high specificities when used with proteins or protein extracts (inhalative allergens, food allergens, insect venoms, latex, and others).

By contrast, results obtained with drugs showed similar specificities but much lower sensitivities below 50% for beta-lactams antibiotics (eg. M. J. Torres, A. Padial, C. Mayorga, T. Fernandez, E. Sanchez-Sabate, J. A. Cornejo-Garcia, C. Antunez, M. Blanca: The diagnostic interpretation of basophil activation test in immediate allergic reactions to betalactams. Clin Exp Allergy 2004, 34, 1768-1775), 12 to 55% for non-steroidal anti-inflammatory drugs (P. Gamboa, M. L. Sanz, M. R. Cabellero, I. Urrutia, I. Antepara, R. Esparza, A. L. de Weck: The flow-cytometric determination of basophil activation induced by aspirin and other non-steroidal anti-inflammatory drugs (NSAIDs) is useful for in vitro diagnosis of the NSAID hypersensitivity syndrome. Clin Exp Allergy 2004, 34 1448-1457) or below 54% for muscle relaxants (eg. N. Abuaf, B. Rajoely, H Ghazouani, D. Levy, C. Pecquet, H Chabane, F. Leynadier: Validation of a flow cytometric assay detecting in vitro basophil activation for the diagnosis of muscle relaxant allergy. J. Allergy Clin Immunol 1999, 104, 411-418), except in patients with perioperative anaphylaxis to muscle relaxants (P. S. Sudheer, J. E. Hall, G. F. Read, A. W. Rowbottom, P. E. Williams: Flowcytometric investigation of peri-anaesthetic anaphylaxis using CD63 and CD203c. Anaesthesia 2005, 60, 251-256). This, however, is not suitable for routine allergy diagnosis.

WO 2007/093517 A1 describes a method and a kit for determining the appearance of adverse reactions in patients in need to undergo to an administration of a pharmaceutical compound. The method for determining potential hypersensitivity in a patient to pseudo-allergic reactions comprises adding a predetermined amount of a compound of anaphylatoxic activity to a sample of the patient's blood and determining the amount of activation of the patient's basophil cells in said blood sample. The compound with anaphylatoxic activity is preferably selected from C3a, C5a, analogs of C3a or C5a, derivatives of C3a or C5a and mixtures thereof. However, this is a very unspecific test, as it does not address the nature of the drug substance potentially causing the anaphylatoxic reaction.

Thus, there is a need for a more sensitive method for allergy diagnosis, in particular for diagnosis of allergies or hypersensitivity to low molecular weight substances such as drugs. J. Sainte-Laudy et al. (Diagnosis of venom allergy by flow cytometry. Correlation with clinical history, skin tests, specific IgE, histamine and leukotriene C4 release. Clin Exp Allergy 2000, 30, 1166-1171) and P. Gane, et al. (Flow cytometric monitoring of allergen induced basophil activation. Cytometry 1995, 19, 361-365) reported that the activation of human basophils led also to a decrease of IgE density on basophil membranes which could be observed by a decrease of the mean fluorescence intensity of the IgE positive cell population (MFI-IgE). In these two documents, the MFI-IgE decrease was observed upon activation with highly allergenic protein extracts from aero-allergens and insect venoms and was just considered as a pharmacological effect on basophilic cells without a use for clinical allergy diagnosis. Based on these observations, two explorative studies have recently been performed to address this phenomenon of IgE down-regulation to drug allergens (J. Sainte-Laudy, A. Boumediene, F. Touraine, I. Orsel, M. Cogné: Analysis of IgE down regulation induced by basophil activation, Application to the diagnosis of muscle relaxant allergic hypersensitivity by flow cytometry. Inflamm Res 2006, 55, Supplement I, S21-S22; J. Sainte-Laudy, F. Touraine, A. Boumediene, F. Bonnaud, M. Cogné: Clinico-biological characteristics of flow cytometry applied to hypersensitivity to NSAIDs. Inflamm Res 2007, 56, Supplement I, S63-S64). It could be shown that in patients with severe allergic reactions (anaphylaxis) to muscle relaxants a CD63 up-regulation (expressed in percentage of basophils showing CD63 expression) was observed in 57% of the cases, while all patients showed a down-regulation of the MFI-IgE. Similarly, 38% of patients with severe adverse reactions to non-steroidal anti-inflammatory drugs (NSAIDs) showed an increase of CD63 expression above the cutoff (positivity threshold) of 5% basophil activation, whereas a significant MFI-IgE down-regulation could be observed in 73% of the same patients. Specificities (control subjects below the cutoff point) were determined to be above 93% in both studies. A severe disadvantage of the method described in these latter two reports is the use of labelled anti-IgE antibodies primarily for positive selection of basophils which contrasts somewhat with its simultaneous use for following basophil activation as determined by IgE down-regulation.

Thus, there is a need for a more reliable method, which provides both high sensitivities and high specificities for drug induced basophil activation, taking into account that basophil activation is a complex process divided in early and late activation events and that basophil labelling with anti-IgE antibodies is currently used for basophil selection and not for determining so basophil activation.

SUMMARY OF THE INVENTION

One object of the invention is to provide a method for the determination of basophil activation induced by a test substance by flow cytometric measurement of the changes of the mean or median fluorescence intensities (MFI) of the basophilic $F_c\epsilon RI$ receptor present on the cell surface of basophils (MFI-$F_c\epsilon RI$) and/or the IgE antibodies bound to said $F_c\epsilon RI$ receptor (MFI-IgE), and the CD63 antigen exposed on the cell surface of basophils after their activation (MFI-CD63), by means of a mixture of anti-CD63, anti-$F_c\epsilon RI$ or anti-IgE, and anti-CCR3 antibodies to each labelled with a distinct fluorophore, of which at least one antibody acts as a basophil selection marker and at least two antibodies act as basophil activation markers, wherein at least one antibody may function both as selection and activation marker, and bringing the changes of the mean fluorescence intensities of said activation markers in correlation to obtain an Activation Index.

A further object of the invention is the provision of an in vitro allergy test comprising the steps of
a) incubating either
   i. an anti-coagulated human or animal whole blood sample, or
   ii. an anti-coagulated and subsequently purified human or animal blood sample
   with a test substance for 5 to 120 minutes, preferably 10-30 minutes, at 30 to 40° C., preferably at 35-38° C., to activate the basophils in said sample,
b) stopping said activation by
   i) adding a stop solution containing EDTA to said sample, or
   ii) putting said sample immediately at 0 to 5° C.,
c) adding to said sample a mixture of antibodies each labelled with a distinct fluorophore, wherein said mixture comprises as labelled antibodies any combination of
   i) anti-CCR3, anti-IgE, anti-$F_c\epsilon RI$, anti-CD45, anti-CD203c, anti-CD123 and anti-HLA-DR, anti-CRTH2 and anti-CD3, basophil specific monoclonal Ba103 antibody, and basophil specific monoclonal 212H6 antibody for basophil selection ("selection marker"), and
   ii) anti-CD63, anti-IgE, anti-$F_c\epsilon RI$, anti-CD203c, anti-CCR3, anti-CD45, anti-CD13, anti-CD69, anti-CD164, and anti-CD107a for basophil activation ("activation marker"), preferably
   I. anti-IgE or anti-$F_c\epsilon RI$ as both selection and activation marker and anti-CD63 as activation marker,
   II. anti-CCR3 as both selection and activation marker and anti-CD63 as activation marker,
   III. anti-CCR3 as selection marker and both anti-CD63 and anti-IgE or anti-$F_c\epsilon RI$ as activation markers,
   IV. anti-CCR3 as selection marker and both anti-CD203c and anti-CD63 as activation markers, and
   V. anti-CD203c as both selection and activation marker and anti-CD63 as activation marker.
   and incubating said sample mixture for 5 to 45 minutes, preferably 10 to 20 minutes, at 2 to 8° C.,
d) lysing remaining erythrocytes in said sample mixture and analysing it on a flow cytometer,
e) measuring the basophil activation, as expressed in changes of the MFI, in said sample mixture induced by said test substance,
f) calculating the basophil Activation Index by correlating the MFI changes.

It is thus another object of the invention to provide a test kit for carrying out said in vitro test, wherein said kit comprises per 100 tests
a) 1 to 5 ml anti-IgE or anti-$F_c\epsilon RI$,
b) 1 to 5 ml anti-CD63, and
c) 1 to 5 ml anti-CCR3, The kit may further comprise per 100 tests 1 to 5 ml of a mixture of antibodies, wherein the mixture comprises as labelled antibodies any combination of
   i) anti-CCR3, anti-IgE, anti-$F_c\epsilon RI$, anti-CD45, anti-CD203c, anti-CD123 and anti-HLA-DR, anti-CRTH2 and anti-CD3, basophil specific monoclonal Ba103 antibody, and basophil specific monoclonal 212H6 antibody for basophil selection, and
   ii) anti-CD63, anti-IgE, anti-$F_c\epsilon RI$, anti-CD203c, anti-CCR3, anti-CD45, anti-CD13, anti-CD69, anti-CD164, and anti-CD107a for basophil activation, preferably
   I. anti-IgE or anti-$F_c\epsilon RI$ as both selection and activation marker and anti-CD63 as activation marker,
   II. anti-CCR3 as both selection and activation marker and anti-CD63 as activation marker,
   III. anti-CCR3 as selection marker and both anti-CD63 and anti-IgE or anti-$F_c\epsilon RI$ as activation markers,
   IV. anti-CCR3 as selection marker and both anti-CD203c and anti-CD63 as activation markers, and
   V. anti-CD203c as both selection and activation marker and anti-CD63 as activation marker.

DETAILED DESCRIPTION OF THE INVENTION

The present invention is based on:
The use of two (instead of just one as used in prior art methods) activation markers such as the MFI-IgE or MFI-$F_c\epsilon RI$ considered as early markers of the basophil activation cascade in addition to the known and single use of CD63 expression or MFI-CD63 which is considered as a later activation marker. In the IgE/CD63 or $F_c\epsilon RI$/CD63 protocols, IgE or $F_c\epsilon RI$ are then considered both as selection and activation markers (see Examples; Protocol 1), whereas in the CCR3/IgE/CD63 or CCR3/$F_c\epsilon RI$/CD63 protocols, IgE or $F_c\epsilon RI$ are then considered as activation markers only, since basophil selection is achieved by the use of CCR3 (see Examples; Protocol 2). IgE or $F_c\epsilon RI$ is down-regulated and CD63 is up-regulated upon basophil activation. The observation of IgE clustering (MFI-IgE decrease) as one of the earliest phenomena of basophil activation is extremely important, since it is established to date that basophil activation may not systematically reach the end point as being represented by the final release of mediators, such as histamine and sulfidoleukotrienes, or by the translocation of CD63 from internal storage granules to the surface of basophils and may, therefore, stop at an intermediate step (J. Rivera, C. Gonzalez-Espinosa, M. Kovarova et al.: The architecture of IgE-dependent mast cell signalling. ACI International 2002, 14, 25-36). Thus, basophil activation upon antigen or allergen stimulation may only be seen by MFI-IgE or MFI-$F_c\epsilon RI$ decrease, but not by a change of CD63 expression. The sensitivity of the method according to the invention, therefore, is markedly improved over existing procedures by the precocity of the analysed marker, specifically MFI-IgE or MFI-F$_c$εRI decrease and MFI-CD63 increase.

The use of a specific algorithm involving both markers the IgE or F$_c$εRI down-regulation being expressed in MFI-IgE or MFI-F$_c$εRI shift and CD63 up-regulation being expressed in MFI-CD63 shift.

This algorithm is obtained from the Activation Indices which can be determined by a 4-parameter-logistic (4-PL) formula of which variables are set in a way that approximatively the same weight is addressed to both MFI-IgE or MFI-F$_c$εRI and MFI-CD63 activation parameters, respectively. Each Activation Index is based on the ratio between the test substance (alternatively, the positive Stimulation Control) and the negative control (Stimulation Buffer). For the MFI-IgE or MFI-F$_c$εRI Activation Index: MFI-IgE or MFI-F$_c$εRI of test substance (alternatively, the positive Stimulation Control) divided by the MFI-IgE or MFI-F$_c$εRI of negative control (Stimulation Buffer); and for the MFI-CD63 Activation Index: MFI-CD63 of the negative control (Stimulation Buffer) divided by the MFI-CD63 of test substance (alternatively, the positive Stimulation Control). The values of said calculation are transformed with a four-parameter logistic (4-PL) function (see example in FIG. 4) in such a way that low ratios turn into low Activation Index values ranging from 0 to 10 and high ratios turn into high Activation Index values ranging from 30 to 500. Most importantly, ratios with medium values around the supposed positivity thresholds are set to fall into the steepest part of the curve as determined by the said mathematical transformation turning into Activation Index values ranging from 10 to 30. The calculation also takes into account outstanding values which may be observed when MFI-IgE or MFI-F$_c$εRI of test substance is lower than MFI-IgE or MFI-F$_c$εRI of negative control (Stimulation Buffer) and, vice versa, values for MFI-CD63 of test substance is greater than MFI-CD63 of negative control (Stimulation Buffer). In both cases, the values related to the test substance are then automatically set to the values observed for the negative control (Stimulation Buffer).

By setting the medium Activation Index values around the supposed positivity thresholds ranging from 10 to 30 to fall into the steepest part of the curve as determined by said transformation, it is possible to improve the clinical sensitivity markedly and to test as positive many patient samples which, otherwise, could not be discriminated from negative control subjects by using the increase of percentage of CD63 expression only (see Examples 9-12).

A further improvement provided by the present invention is that the results obtained are independent of the type of flow cytometer and test reagents used.

The use of a stable and constitutively expressed basophil selection marker, such as the chemokine receptor 3, CCR3, as an independent marker which is not influenced by the stimulation of a test substance, leads to a better and easier discrimination of the basophilic cells (see example 6). This improved basophil selection procedure simplifies the basophil gating over existing methods using either IgE (EP 0 974 050 B1) or CD203c (WO 03/025566 A2) as selection markers.

Thus, the present invention provides new methods for the determination of basophil activation induced by a test substance by flow cytometric measurement of the changes of the mean or median fluorescence intensities (MFI) of the basophilic F$_c$εRI receptor present on the cell surface of basophils (MFI-F$_c$εRI) or the IgE antibodies bound to said F$_c$εRI receptor (MFI-IgE), and the CD63 antigen exposed on the cell surface of basophils upon their activation (MFI-CD63), by using a mixture of anti-CD63, anti-F$_c$εRI or anti-IgE, and anti-CCR3 antibodies each labelled with a distinct fluorophore, of which at least one antibody acts as a basophil selection marker and at least two antibodies act as basophil activation markers, wherein at least one antibody may function both as selection and activation marker, and bringing the changes of the mean fluorescence intensities of said activation markers in correlation to obtain a combined Activation Index.

The Activation Index (AI) is defined as the product of the values either related to MFI-CD63 (A) or to MFI-IgE (B) or to MFI-F$_c$εRI (B) transformed to $$y = \frac{a-d}{\left(1+\left(\frac{x}{c}\right)^b\right)} + d$$

wherein
i) a is defined as the minimum value of the function curve,
ii) b is defined as the slope of the curve,
iii) c is defined as the turning point of the curve,
iv) d is defined as the maximum asymptotic value of the curve,
v) x is defined as either 1 minus the ratio between (A) of the negative control and (A) of the test substance (alternatively, (A) of the positive Stimulation Control (=MFI-CD63 of negative control divided by MFI-CD63 of test substance or, alternatively, of positive Stimulation Control) or 1 minus the ratio between (B) of the test substance (alternatively, (B) of the positive Stimulation Control) divided by (B) of the negative control (=MFI-IgE or MFI-F$_c$εRI of test substance or, alternatively, of the positive Stimulation Control divided by the MFI-IgE or MFI-F$_c$εRI of negative control), and
vi) y is defined as the Activation Index of (A) or (B)

A combined Activation Index can be calculated by addition of y(A) and y(B) or by multiplying y(A) with y(B).

The method needs basophil staining by a mixture of antibodies each labelled with a distinct fluorophore, such as, but not limited to, fluorescin isothiocyanide (FITC), phycoerythrin (PE), APC, Cy3, Cy5, Alexa dyes such as AlexaFluor 647, and Dyomics dyes such as DY-647 or DY-747.

This mixture comprises as labelled antibodies any combination of
i) anti-CCR3, anti-IgE, anti-F$_c$εRI, anti-CD45, anti-CD203c, anti-CD123 and anti-HLA-DR, and anti-CRTH2 and anti-CD3, basophil specific monoclonal Ba103, and basophil specific monoclonal 212H6 antibodies for basophil selection, and
ii) anti-CD63, anti-IgE, anti-F$_c$εRI, anti-CD203c, anti-CCR3, anti-CD45, anti-CD13, anti-CD69, anti-CD164, and anti-CD107a for basophil activation, preferably
I. anti-IgE or anti-F$_c$εRI as both selection and activation marker and anti-CD63 as activation marker,
II. anti-CCR3 as both selection and activation marker and anti-CD63 as activation marker,
III. anti-CCR3 as selection marker and both anti-CD63 and anti-IgE or anti-F$_c$εRI as activation markers,
IV. anti-CCR3 as selection marker and both anti-CD203c and anti-CD63 as activation markers, and V. anti-CD203c as both selection and activation marker and anti-CD63 as activation marker.

Preferably, this mixture comprises as labelled antibodies:
anti-IgE and anti-CD63
anti-F$_c$εRI and anti-CD63
anti-CCR3 and anti-IgE and anti-CD63
anti-CCR3 and anti-F$_c$εRI and anti-CD63
anti-CCR3 and anti-CD63
anti-CCR3 and anti-IgE
anti-CCR3 and anti-F$_c$εRI.
anti-CD 203c and anti-CD63
anti-CD203c and anti-CD63 and anti-CCR3

The test substance is preferably a mitogen, an antigen, an allergen, a protein or peptide, a protein or peptide allergen, a group or mixture of protein and/or peptide allergens, a non-proteinaceous allergen, a low molecular weight allergen, a low molecular weight drug substance or a hapten. Most preferred the test substance is an antigen, hapten or allergen, wherein the antigen, hapten or allergen is a low molecular weight substance below 1000 Da.

The increase in sensitivity using the presented invention is much more significant for drugs and other low molecular weight sbstances than for proteinaceous allergens or petides as, for these latter allergens, the state of the art methods using percentage of CD63 activation generally reach high sensitivities (eg. M. L. Sanz, J. P. Maselli, P. M. Gamboa, A. Oehling, I. Diéguez, A. L. de Weck: Flow cytometric basophil activation test: a review. J Investig Allergol Clin Immunol 2002, 12, 143-154; D. G. Ebo, J. Sainte-Laudy, C. H. Bridts, C. H. Mertens, M. M. Hagedorens, A. J. Schuerwegh, L. S. de Clerck, W. J. Stevens: Flow-assisted allergy diagnosis: current applications and future perspectives. Allergy 2006, 61, 1028-1039).

Preferably, the drug substance is selected from the group consisting of antibiotics and antimycotics, antiseptics, antiviral agents, anti-malarial agents, analgesics and non-steroidal anti-inflammatory drugs (NSAIDs), pain releasers such as COX-2 inhibitors, neuromuscular blocking agents (NMBs), hypnotics and local anesthetics, tranquilizers, opioids, radio contrast media, proton pumping inhibitors (PPIs), anticonvulsants and neuroleptics, anti-psychotic agents, anti-depressants, dopamins, anti-histamines, corticosteroids and glucocorticoids, chemotherapeutic and immunosuppressive agents, diuretics, anticoagulants, vasoconstrictors, cardiac drugs, (anti-)ulcer drugs, (anti-)thyroid drugs, estrogens, aprotinines, heparins and derivatives, insulin preparations, streptokinases and urokinases, interferons and interleukins, anti-immunoglobulin E (Xolair) and any other drug causing adverse drug reactions or drug hypersensitivities.

Suitable penicillins and β-lactams antibiotics are, but not restricted to, Penicillin G, Penicillin V, PPL, MDM, Amoxicillin, Ampicillin, Flucloxacillin, Methicillin, Oxacillin, Cloxacillin, Dicloxacillin, Nafcillin, Carbenicillin, Ticarcillin, Mezlocillin, and Piperacillin.

Suitable cephalosporibns are, but not restricted to, Cephalosporin C, Cephalotin, Cefazolin, Cefalexin, Cefadroxil, Cefamandole, Cefoxitin, Cefaclor, Cefuroxime, Loracarbef, Cefonicid, Cefotetan, Cefonaride, Ceftriaxone, Cefpodoxime, Cefixime, Cefoperazone, Cefotaxime, Ceftazidime, Cephalexin, Cephaloridine, Cephapirin, Cephradine, Ceftibuten, Cefcapen pivoxil and Cefepime.

Suitable β-lactamase inhibitors are, but not restricted to, Cilastatin, Tazobactam and Clavulanic acid.

Suitable carbapenem antibiotics are, but not restricted to, Imipenem and Meropenem.

Suitable monobactam antibiotics are, but not restricted to, Aztreonam.

Suitable sulfonamide antibiotics are, but not restricted to, Sulfomethoxazole.

Suitable quinolone antibiotics are, but not restricted to, Fluoroquinolone, Ciprofloxacin, Ofloxacin, Lomefloxacin, Norfloxacin, Moxifloxacin and Levofloxacin.

Suitable imidazole antibiotics are, but not restricted to, Ketoconazole, Fluconazole and Amphotericin B.

Suitable tetracyclin antibiotics are, but not restricted to, Minocyclin, Doxycycline Oxytetracycline and Tetracycline.

Suitable glycopetide antibiotics are, but not restricted to, Vancomycin and Teicoplanin.

Suitable polypeptide antibiotics are, but not restricted to, Bacitracin, Colistin, and Polymyxin B.

Suitable rifamycin antibiotics are, but not restricted to, Rifampicin and Rifamycin.

Suitable aminoglycoside antibiotics are, but not restricted to, Streptomycin, Tobramycin, Neomycin B, Amikacin, and Gentamicin.

Suitable macrolide antibiotics are, but not restricted to, Erythromycin, Azithromycin, Clarithromycin, Spiramycin, Roxithromycin, Fosfomycin and Telithromycin.

Suitable streptogramin antibiotics are, but not restricted to, Pristinamycin.

Suitable nitrofuran antibiotics are, but not restricted to, Nitrofurantoin.

Suitable other antibiotica classes are, but not restricted to, pyrazolones isoniazides and pentamidines.

Suitable other antiobiotics are, but not restricted to, Chloramphenicol, Metronidazole, Minocyclin, Clindamycin, Kanamycin, Lincomycin, Josamycin, Trimethoprim, Terbinafin, Fusafungine, Metronidazole, Ethambutol, Cefoperazone, Griseofulvin, Piromidic acid, Quinine and Nystatin.

Suitable antiseptics are, but not restricted to, Chlorhexidine and Povidone-iodine.

Suitable antiviral agents are, but not restricted to, Lamivudine, Nevirapine, Foscarnet, Abacavir, Acyclovir, Atazanavir, Famciclovir, Gangcyclovir, Indinavir and Valaciclovir.

Suitable anti-malarial agents are, but not restricted to, Amodiaquine, Chloroquine, Quinacrine and other quinines.

Suitable analgesics and non-steroidal anti-inflammatory drugs (NSAIDs) are, but not restricted to, Aspirin, Lys-Aspirin, Ibuprofen, Ketoprofen, Fenoprofen, Flurbiprofen, Pirprofen, Diclofenac, Naproxen, Paracetamol (Acetaminophen), Dipyrone (Metamizol), Sulfasalazine, Sulfinpyrazone, Indomethacin, Mefenamic acid, Phenylbutazone, Phenazone, Propyphenazone, Aminophenazone, Tiaprofenic acid, Glafenin, Ketorolac, Etodolac, Sulindac, Alclofenac, Fenclophenac, Zomepirac, Mesalazine, Niflumic acid, Tolmetin, Meclofenamate, Diflunisal, Nabumetone, Tramadol, Tenoxicam, Oxaprocin, Meloxicam and Piroxicam.

Suitable COX-2 inhibitors are, but not restricted to, Nimesulide, Meloxicam, Celecoxib, Etoricxib, Valdecoxib and Rofecoxib.

Suitable NMBs (neuromuscular blockers or muscle relaxants) are, but not restricted to, Suxamethonium, Atracurium, Cis-atracurium, Alcuronium, Mivacurium, Pancuronium, Rocuronium, Vecuronium, Decamethonium, Rapacuronium, Gallamine, Succinylcholine and Curare.

Suitable hypnotics and local anesthetics are, but not restricted to, Etomidate, Ketamine, Midazolam, Propofol, Thiopental, Alfentanil, Fentanyl, Remifentanil, Sufentanil, Zopiclone, Lidocaine, Bucivapaine, Mepivacaine, Propoxycaine hydrochloride, Xylocalne and Ropivacaine.

Suitable tranquilizers are, but not restricted to, Clobazam, Tetrazepam and Diazepam.

Suitable opioids are, but not restricted to, Methadone, Pethidine, Oxycodone hydrochloride, Codeine and Morphine.

Suitable radio contrast media are, but not restricted to, Iothalamate, Ioxithalamate, Amidotriozate, Iohexol, Iopentol, Iomeprol, Ioversol, Iopromide, Iobitridol, Iopamidol, Ioxitol, Iotrolan, Iodixanol, Ioxaglate, Gd-DOTA, Isosulfan Blue, Patent Blue and Methylene Blue.

Suitable PPIs (proton pumping inhibitors) are, but not restricted to, Omeprazole, Pantoprazole, Esomprazole, Lansoprazole and Rabeprazole.

Suitable anticonvulsants and neuroleptics are, but not restricted to, Carbamazepine, Lamotrigine, Oxcarbazepine, Chlorprothixene, Phenobarbital, Felbamate, Mesantoin, Phenytoin and Valproic acid.

Suitable anti-psychotic agents are, but not restricted to, Chlorpromazine, Prochloperazine, Clozapine, Meprobamate and Mianserin.

Suitable antidepressants are, but not restricted to, Doxepin, Fluoxetine, Sertraline, and Paroxetine.

Suitable dopamins are, but not restricted to, $\alpha$-Methyldopa and L-Dopa.

Suitable anti-histamines are, but not restricted to, Cimetidine, Ceftrizine, Chlorpheniramine, Ranitidine, Olopatadine, Ketotifen, Azelastine, Fexofenadine, Loratidine, Desloratidine, Levocabastine, Emedastine and Epinastine.

Suitable corticosteroids and glucocorticoids are, but not restricted to, Hydrocortisone, Dexamethasone, Beclometasone, Prednisolone, Methylprednisolone, Disodium Chromoglycate, Nedocromil, Lodoxamide, and Triamincinolone.

Suitable chemotherapeutic and immunosuppressive agents are, but not restricted to, Cisplatin, Carboplatin, Oxaliplatin, Cyclophosphamide, Tacrolimus, Tamoxifen, Azathioprin and cyclosporines.

Suitable diuretics are, but not restricted to, Furosemide, Bumetadine, Chlorthalidone, Ethacrynic acid, Hydrochlorthiazide, Indapamide, Tienilic acid, Trimetrene and Torsemide.

Suitable anticoagulants are, but not restricted to, Warfarin, Fluindione, Phenindione and Phenprocoumon.

Suitable vasoconstrictors are, but not restricted to, Antazoline, Naphazoline and Chlorpheniramine.

Suitable cardiac drugs are, but not restricted to, statins (Atorvastatin, Simvastatin), ACE inhibitors (Captopril, Ramipril, Enalapril), alpha-receptor blockers (Urapidil, Tamsulosin), beta-receptor blockers (Metoprolol, Bisoprolol, Nebivolol, Ambroxol, Propranolol), calcium antagonists (Diltiazem) and anti-hypertonic agents (Clopidogrel, Candesartan).

Suitable (anti-)thyroid drugs are, but not restricted to, L-thyroxin, Levothyroxine, Carbimazole, Methimazole, Propylthiouracil and Thiocyanate.

Suitable (anti-)ulcer drugs are, but not restricted to, Ranitidine, Cimetidine and Misoprostol.

Suitable other drugs are, but not restricted to, estrogens, insulins, Allopurinol, Acetylcholine, Acetylcysteine, Thiamazol, Mexiletine hydrochloride, Dapsone, Hydroxycine, Calcipotriol, Ciproheptadine, Domperidone, Salbutamol, Nedocromil, Colchicine, Cyamethazine, Enoxoparin, Bumadizon, Amlopidine, Antrafenin, Bethanidine, is Chlorpropamide, Clofibrate, Fenofibrate, Clometacin, Disulfiram, Famotidine, Flocatfenin, Glafenin, Leflunomid, Nicergolin, Rosiglitazone, Pamidronate, Phenothiazine, Phenylpropanolamine, Piperazine hydrate, Probenecid, Montelukast, Pranlukast, Aminopyrine and other pyrazolones.

The allergen may also be a food additive. Preferably, the food additive is selected from the group consisting of food preservatives, food colorants, food finishers, anti-oxidants, and emulsifiers.

Suitable food additives are, but not restricted to, Sodium benzoate, p-Hydroxy-Benzoate, Methylhydroxy-Benzoate, Propylhydroxy-Benzoate, Sodium nitrite, Sodium sulfites, Potassium metabisulfite, Sodium salicylate, Butylhydroxyanisol, Butylhydroxytoluene, Propylgallate, Caffeic acid, Glutamate, Tartrazine, Quinoline Yellow, Sunset Yellow FCF, Chromotrope 2B, Amaranth, New Coccine, Erythrosine, Patent Blue V, Indigo Carmine, Brillant Black BN, Azorubin, Ponceau 4R, Aspartam, Ascorbic acid (Vitamin C), $\alpha$-Tocopherol (Vitamin E) and Vitamin K.

The allergen may also be a colloid, plasma expander or auxiliary agent. Suitable colloids, plasma expanders or auxiliary agents are, but not restricted to, Albumin, Dextran, Gelatine, Hetastarch, Pentastarch, Sinistrin, Polydocanol 600 (Ethoxysclerol), Lactose, Carboxymethylcellulose, Hydroxypropylcellulose, Protamine and Aprotinin.

The allergen may also be an occupational, environmental or pollutant agent and any other chemical used in the food, baking, washing or textil industry with a potential of causing adverse drug reactions.

Suitable occupational, environmental or pollutant agents are, but not restricted to, isocyanates, isothiazolinones, Formaldehyde, Ethylene oxide, Phthalic anhydride, Chloramine T, DMSO, Latex, and enzymes used in the baking, food processing and washing industry.

The allergen may also be a protein or a mixture of proteins or a protein extract from a biological source, preferably selected from the group of insect venoms, foods (fruits, vegetables, seeds, legumes, nuts, spices, fish, shellfish, mollusks, egg, fowl, meat and milk), tree pollens, grass pollens, weed pollens, epidermals and animal proteins, dust and storage mites, insects, parasites, microorganisms and house dusts.

The amount of test substance, preferably of an allergen, is preferably in the range of 0.1 ng/ml to 10 mg/ml.

In contrast to prior art methods, the blood is anticoagulated with EDTA instead of heparin or citrate (ACD). The benefit of anticoagulation with EDTA is in the enhanced stability of blood samples and basophilic cells for up to 3 days as compared with other anticoagulants (see Example 1).

In contrast to prior art methods, which use either a bully coat or undiluted whole blood, the analysis is carried out either with a diluted whole blood sample or a purified blood sample without the need of its concentration before the stimulation reaction (see Example 2).

The whole blood is diluted 2-fold to 10-fold, preferably 4-fold, with the cellular incubation buffer (Stimulation Buffer). The benefit of this dilution step is in i) the prevention of inhibitory effects which can be observed when using undiluted whole blood, and ii) the requirement of a rather small volume of blood, preferably when analysing samples from newborns, babies or small children.

The blood sample is washed by low speed centrifugation replacing the plasma fraction containing thrombocytes and potentially interfering factors. The benefit of this washing step is i) to enhance the basophil reactivity with weak stimulators such as certain drug substances, ii) to avoid any putative plasma interference, and iii) to measure basal basophil reactivity (i.e. in the absence of potentially interfering (IgG) antibodies in the follow up of patients undergoing a specific immunotherapy as demonstrated for hymenoptera venoms (see Example 5).

The diluted whole blood sample or the purified blood sample preferably has a volume between 10 and 200 µl, more preferably 20 to 50 µl. Therefore, in contrast to prior art methods, a rather small volume of blood is sufficient, preferably when analysing samples from newborns, babies or small children.

The incubation is preferably carried out in the range of from 30 to 40° C., most preferably at 37° C. The activation is preferably stopped by adding a stop solution containing 1 to 10 mmol/l of EDTA, preferably 2 mmol/l.

It is further preferred that before step a) interleukin-3 is added to the whole blood sample or the purified blood sample. Preferably, the interleukin-3 is added in an amount resulting in a concentration range of 0.2 to 20 ng/ml, most preferably 2 ng/ml (see Example 4).

With the purified blood sample protocol, it is further preferred that no lysis step d) of erythrocytes is performed (see Example 3). The absence of the lysis step d) involves a simplification of the entire process and allows for an automation of the test. Thereby, it is possible to run the test 24 hours a day. Still further, the lysis step is critical since the cells are rather sensitive to this step.

In a third embodiment the present invention provides a kit for an in vitro allergy test as described in the context with the second embodiment of the present invention, wherein said kit comprises per 100 tests
  a) 1 to 5 ml anti-IgE or anti-$F_c\epsilon RI$,
  b) 1 to 5 ml anti-CD63, and
  c) 1 to 5 ml anti-CCR3,
  wherein said kit may comprise further per 100 tests 1 to 5 ml of a mixture of antibodies, wherein the mixture comprises as labelled antibodies any combination of
    i) anti-CCR3, anti-IgE, anti-$F_c\epsilon RI$, anti-CD45, anti-CD203c, anti-CD123 and anti-HLA-DR, anti-CRTH2 and anti-CD3, basophil specific monoclonal Ba103 antibody, and basophil specific monoclonal 212H6 antibody for basophil selection, and
    ii) anti-CD63, anti-IgE, anti-$F_G\epsilon RI$, anti-CD203c, anti-CCR3, anti-CD45, anti-CD13, anti-CD69, anti-CD164, and anti-CD107a for basophil activation, preferably
      I. anti-IgE or anti-$F_c\epsilon RI$ as both selection and activation marker and anti-CD63 as activation marker,
      II. anti-CCR3 as both selection and activation marker and anti-CD63 as activation marker,
      III. anti-CCR3 as selection marker and both anti-CD63 and anti-IgE or anti-$F_c\epsilon RI$ as activation markers,
      IV. anti-CCR3 as selection marker and both anti-CD203c and anti-CD63 as activation markers, and
      V. anti-CD203c as both selection and activation marker and anti-CD63 as activation marker.

The kit may comprise additionally up to 200 ml of a cellular incubation buffer (the Basophil Stimulation Buffer). The cellular incubation buffer is selected from basophil activation buffers which contain an optimum calcium and magnesium concentration in optimized physicochemical conditions. The cellular incubation buffer preferably contains additionally 0.2 to 20 ng/ml of interleukin-3, 0.5 to 10 mmol/l of calcium ions, and 0.01 to 0.5% of heparin (w/v). The cellular incubation buffer is used for diluting the blood samples and test substance(s) as well as for the activation step.

The kit preferably comprises additionally up to 5 ml of a Stimulation Control. The Stimulation Control is selected from the groups of anti-IgE antibody, anti-FcεRI antibody, N-formyl-L-methionyl-L-leucyl-L-phenylalanine (fMLP), complement factor 5a (C5a), platelet activation factor (PAF), toll-like receptor (TLR) agonists, ionomycin, calcium ionophore A23187, lipopolysaccharides (LPS) and phytohaemagglutinins (PHA), More preferably, the kit comprises an anti-FcεRI antibody or fMLP or a mixture thereof as the Stimulation Control. Most preferably, the kit comprises an anti-FcεRI antibody as the Stimulation Control.

The kit preferably comprises additionally up to 500 ml of a Lysing Reagent. Suitable lysing reagents are preferably selected from any kind of erhythrocyte lysing buffers known from prior art.

The kit preferably comprises additionally up to 200 ml of a Wash Buffer. Suitable wash buffers are preferably selected from any kind of wash buffers known from prior art to neutralize the effect of the Lysing Reagent and to eliminate disturbing factors and cell debris after erythrocyte lysis.

The kit preferably comprises additionally up to 500 ml of a Blocking Buffer. Suitably blocking buffers are selected from any kind of buffers known from prior art. The Blocking Buffer preferably contains additionally 0.5 to 10 mmol/l of EDTA.

The measurement of the mean or median fluorescence intensity (MFI) by flow cytometry is carried out as known from the prior art (eg. H. M. Shapiro: Practical flow cytometry—$4^{th}$ ed., 2003. John Wiley & Sons, Inc., Hoboken, N.J.).

Additionally, the kit is preferably delivered with an unlimited number of vials containing 0.1 ng to 10 mg of a test substance.

Prior art methods have shown that the basophil activation induced by drugs is sometimes rather weak. Therefore, it has been suggested to use for the analysis an early activation marker, such as the decrease of MFI-IgE, together with the increase of a late activation marker, such as CD63 (J. Sainte-Laudy, A. Boumediene, F. Touraine, I. Orsel, C. Brianchon, F. Bonnaud, M. Cogné: Use of both CD63 up reguation and IgE down regulation for the flowcytometric analysis of allergen induced basophil activation. Definition of an activation index. Inflamm. Res. 2007, 56, 1-6). This paper represents the definition of a linearized-logarithmic activation index of MFI-IgE, sometimes combined with the percentage of CD63 expression. It shows that the use of an early marker, such as IgE, in parallel with the rather late CD63 marker leads to an increase in sensitivity of the flow cytometric methods applied to the diagnosis of allergy to beta-Lactam antibiotics without decreasing its specificity.

However, as can be seen from the Examples section, also this combination does not give a sufficiently high sensitivity, particularly when looking at only one allergen in only one concentration for a certain class of drugs such as NSAIDs or β-lactam antibiotics. This can only be achieved by calculating the MFI-IgE or MFI-$F_c\epsilon RI$ Activation Index, the MFI-CD63 Activation Index and, preferably, the combined MFI-IgE/MFI-CD63 Activation Index, respectively (see Examples 9-11).

Without the wish to being bond to theory, it is believed, that non-proteinaceous, low molecular weight allergens have too little epitopes and are therefore rather weak allergens. They may be even haptens, i.e. causing an immune response only when attached to a large carrier such as a protein.

The use of two particular combinations of the three activation markers IgE, $F_c\epsilon RI$ and CD63 according to the present invention allows to measure the changes in MFI by a flow cytometric method, to calculate an Activation Index by an algorithm based on said MFI changes, and to compare said Activation Index or Activation Indices with a clinical suspicion in a patient, therefore confirming or disproving an allergic or hypersensitivity reaction to one or several test substance(s) as defined by the Activation Index number(s) above or below the positivity threshold (cutoff).

The Activation Index is defined as the product of the values either related to MFI-CD63 (A) or to MFI-IgE (B) or to MFI-$F_c\epsilon$RI (B) transformed to $$y = \frac{a-d}{\left(1+\left(\frac{x}{c}\right)^b\right)} + d$$

wherein
i) a is defined as the minimum value of the function curve,
ii) b is defined as the slope of the curve,
iii) c is defined as the turning point of the curve,
iv) d is defined as the maximum asymptotic value of the curve,
v) x is defined as 1 minus the ratio between (A) of the negative control and (A) of the test substance or, alternatively, (A) of the positive control (MFI-CD63 of negative control divided by MFI-CD63 of test substance or, alternatively, of positive control) or 1 minus the ratio between (B) of the test substance or, alternatively, (B) of the positive control and (B) of the negative control (MFI-IgE/$F_c\epsilon$RI of test substance or, alternatively, of positive control divided by MFI-IgE/$F_c\epsilon$RI of negative control), and
vi) a combined Activation Index is calculated by addition of y(A) and y(B) or by multiplying y(A) with y(B).

This algorithm is based on the calculation of Activation Indices which can be determined by a 4-parameter-logistic (4-PL) formula of which variables are set in a way that approximatively the same weight is addressed to both MFI-IgE or MFI-$F_c\epsilon$RI and MFI-CD63 activation parameters, respectively (see example in Table 1). Each Activation Index is based on the ratio between the test substance (alternatively, the positive Stimulation Control) and the negative control (Stimulation Buffer): MFI-IgE or MFI-$F_c\epsilon$RI of test substance (alternatively, positive Stimulation Control) divided by MFI-IgE or MFI-$F_c\epsilon$RI of negative control (Stimulation Buffer), and MFI-CD63 of negative control (Stimulation Buffer) divided by MFI-CD63 of test substance (alternatively, positive Stimulation Control), respectively. The calculation also takes into account outstanding values which may be observed when MFI-IgE or MFI-$F_c\epsilon$RI of test substance is lower than MFI-IgE or MFI-$F_c\epsilon$RI of negative control (Stimulation Buffer) and, vice versa, value for MFI-CD63 of test substance is greater than MFI-CD63 of negative control (Stimulation Buffer). In both cases, the values related to the test substance are then automatically set to the values observed for the negative control (Stimulation Buffer).

Results obtained by this calculation method are also independent of the is reagents and of the type of flow cytometer instrument used as the (A) and (B) values are included as ratios.

The calculation may be performed by means of a computer. Thus, the present invention also provides a software package for the calculation of the said basophil Activation Indices.

The dimensionless, arbitrary value obtained for the Activation Index may range between 0 and 500 depending on the setting of above variables "a" and "d" (see example in Table 1). A positive test shows a value of the Activation Index of greater than 6 up to 30 for low molecular weight substances such as drug allergens and of greater than 100 for protein allergens. In order to obtain the optimum positivity threshold (cutoff point), the Activation Index may be determined for each test substance and each concentration by Receiver Operator Characteristics (ROC) curves employing clearly defined allergic patients compared to non-allergic control subjects (see Example 8).

BRIEF DESCRIPTION OF THE DRAWINGS

FIG. 1A shows setting of a gate 1 (R1) by including the entire lymphocyte population. FIG. 1B shows the brightly fluorescent FITC cells (IgE positive cells) within the lymphocyte population gate (R2). FIG. 1C shows calculation of the percentage of brightly fluorescent PE cells (CD63 positive cells) compared to the total amount of brightly fluorescent FITC cells, by the cytometer software.

FIG. 3A shows setting of a gate 1 (R1) by including the entire basophil population CCR3$^{pos}$ with low Side Scatter SSC. FIG. 3B shows calculation of the percentage of CD63 positive cells (brightly fluorescent FITC; Q2) compared to the total amount of basophilic cells gated in R1. FIG. 3C shows calculation of the percentage of brightly fluorescent FITC cells (CD63 positive cells) and brightly fluorescent AlexaFluor 647 cells (IgE positive cells; FIG. 3B), respectively, calcaluted by the cytometer software.

FIG. 5 shows experiments with patients.

FIG. 7 A shows reaction of basophils from washed blood to a 25-fold lower concentration of bee venom extract.

FIG. 8 shows effects of allergens on the stimulation of or cytotoxicity of blood basophils.

FIG. 9 shows that a combination of stimulation Protocol 2 and the CCR3 basophil selection marker makes it possible to simplify, speed up and/or automatize the process.

FIG. 10 shows results of Example 6 (advantages of using CCR3 as selection marker as compared to IgE).

FIG. 11 shows results of Example 7 (alternative use of FcεRI instead of IgE).

FIG. 12 shows results of Example 8 (ROC curves for NSAIDs allergens).

Figure 1:
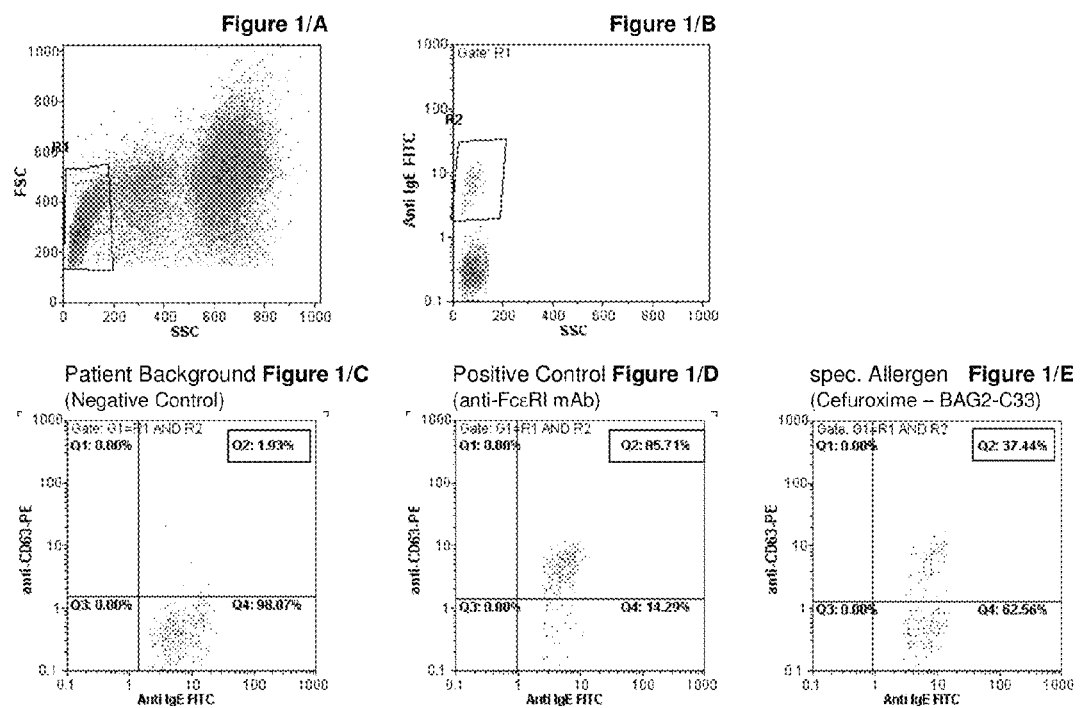
FIG. 1 shows a three step analytical procedure.

The invention is now further illustrated by several non-limiting Examples.

EXAMPLES

When not otherwise indicated the examples were performed with one of the two following protocols.
Protocol 1: IgE-FITC/CD63-PE
1.1 Principle of the Assay Peripheral blood leukocytes are isolated from patients' whole blood samples and primed with Stimulation Buffer containing interleukin 3 (IL-3). Specific allergen is added and the cells are incubated to mimic the in vivo situation where, in IgE mediated allergies, specific IgE bound to the cellular surface are bridged by the allergen and activate an intracellular enzymatic cascade leading to the activation of the basophils, but also so-called non-IgE mediated allergies, which are particularly observed with certain drugs, may lead to the same phenomenon on basophils. During this activation intracellular compounds containing the transmembrane protein CD63 are fused to the cellular membrane and therefore exposed to the extracellular matrix.

A highly specific monoclonal antibody (mAb) recognizing the high affinity IgE binding receptor (FcεRI) is used as a positive control, leading to the activation of the basophils by mimicking the bridging event.

After stopping the reaction the Staining Reagent is added containing a mixture of monoclonal antibodies to human CD63 labeled with phycoerythrin (anti-CD63-PE) and to human IgE labeled with fluorescein isothiocyanate (anti-IgE-FITC). The remaining erythrocytes are removed by a lysing reaction and after blocking the reaction the cells are analyzed by flow cytometry.

1.2 Reagents

| Stimulation Buffer with heparin and IL-3 | 1 vial lyoph. | Reconstitute with 50 ml of $H_2O$ |
|---|---|---|
| Stimulation Control anti-FcεRI mAb | 1 vial lyoph. | Reconstitute with 1.5 ml of $H_2O$ |
| Staining Reagent Mix of anti-CD63-PE and anti-IgE-FITC mAb | 1 vial 2.2 ml | Ready to use |
| Lysing Reagent 10x concentrated | 1 vial 40 ml | Dilute with 360 ml of deionized $H_2O$ |
| Blocking Buffer stop of cell lysis | 2 vials 100 ml | Ready to use |
| Protein Allergen | 1 vial (1 μl) | Dilute with 250 μl Stimulation Buffer |
| Low Molecular Weight (Drug) Allergen | 1 vial lyoph. | Dilute with 250 μl Stimulation Buffer |

1.3 Assay Procedure
1. Mix the anti-coagulated blood sample by inverting the venipuncture tube several times. Centrifuge the venipuncture tube for 5 minutes at 200×g. After the centrifugation step, two phases can be observed from top to the bottom of the tube:
   i) plasma fraction containing the leukocytes
   ii) erythrocyte fraction
   Alternative procedure for cell separation:
   Mix the anti-coagulated blood sample by inverting the venipuncture tube several times.
   Let the samples sediment (erythrocytes) at room temperature for one hour. Collect the upper phase (plasma fraction containing the leukocytes) and continue with step 2.
   If the erythrocytes sedimentation is not complete after one hour of incubation, the centrifugation step above is recommended.
2. Collect the plasma fraction with the leukocytes on the top of the erythrocytes with a disposable plastic syringe or plastic pipette and transfer it into a fresh and pyrogen-free 5 ml polypropylene or polystyrene tube.
   NOTE: Because of the low amount of basophils in the leukocyte fraction it is important to collect the entire plasma fraction. Contamination with a low amount of erythrocytes does not significantly influence the results.
3. Centrifuge for 10 minutes at 500×g. Completely remove the plasma fraction on the top of the cell pellet with a pipette.
4. Add 100 μl of Stimulation Buffer per ml of blood used at the beginning (i.e. for 5 ml blood sample used, the pellet has to be solved with 500 μl of Stimulation Buffer). Resuspend the leukocytes pellet carefully.
5a. For each patient, label pyrogen-free polystyrene tubes suited for Flow Cytometry measurements (e.g., PB=patient background=negative control, PC=stimulation control with anti-FcεRI Ab, A1-1 for antigen 1 with dilution 1, A1-2 for allergen 1 with dilution 2, etc.) or use tissue culture grade microtiter plates.

5b. Pipet 50 μl of Stimulation Buffer (background 0 negative control) into the PB tube of each patient.

5c. Pipet 50 μl of Stimulation Control into the PC tube of each patient.

5d. Pipet 50 μl of Allergen (=test substance) into the corresponding patient tubes.

6. Pipet 50 μl of each patient's cell suspension into the corresponding tubes.

7. Vortex gently, cover the tubes and incubate for 40±5 minutes at 37° C. in a water bath.

8. Add 50 μl of cold Blocking Buffer to each tube.

9. Add 20 μl of cold Staining Reagent to each tube. Vortex gently.

10. Incubate for 30±5 minutes at 2-8° C.

11. Vortex gently the sedimented cells, add 3.5 ml of pre-warmed (18-28° C.) Lysing Reagent to each tube and incubate for 5±1 minutes at 18-28° C.

12. Stop the reaction with 1 ml of Blocking Buffer.

13. Centrifuge for 5 minutes at 1000-1200×g.

14. Decant or aspirate the supernatant and resuspend the cell pellet with 500 μl of Blocking Buffer. Vortex gently.

15. Proceed to the analysis by Flow Cytometry within 2 hours.

1.4 Flow Cytometry

Flow cytometric analysis can be performed on any flow cytometer containing a 488 nm argon laser (blue-green excitation light) and the corresponding software.

At least 150 basophilic cells must be analyzed, requiring a total amount of 50,000 to 80,000 leukocytes to analyze. Because of the lower activation percentage in drug allergies, the lower limit of basophilic cells to be analyzed should be set to 200 or more.

Figure 2:
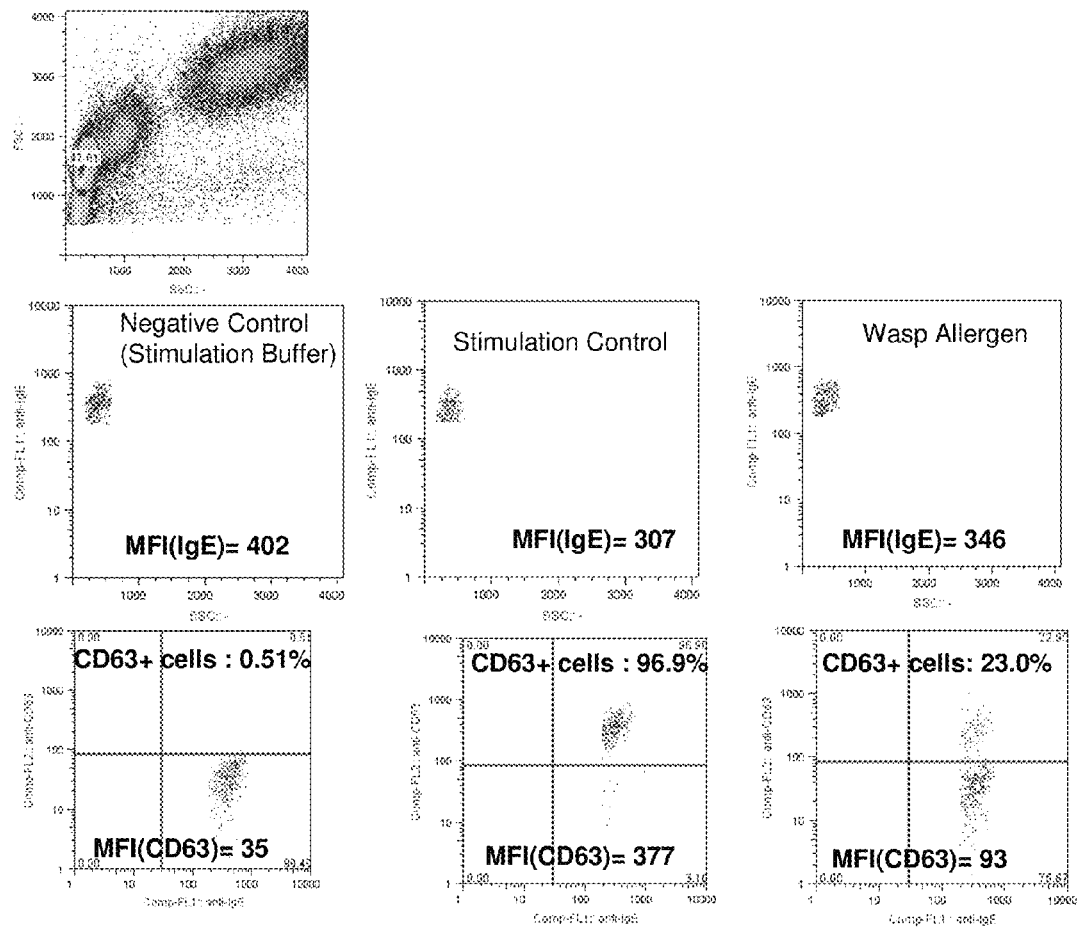
FIG. 2 shows a reading of the MFI values and MFI shifts for brightly fluorescent FITC cells (IgE positive cells) and brightly fluorescent PE cells (CD63 positive cells), respectively, calcaluted by the cytometer software.

The analysis is based on three steps (see FIG. 1):

1. Set a gate 1 (R1) by including the entire lymphocyte population (FIG. 1/A).
2. Within the lymphocyte population gate (R2) the brightly fluorescent FITC cells (IgE positive cells) (see FIG. 1/B).
3a. Calculate the percentage of brightly fluorescent PE cells (CD63 positive cells) compared to the total amount of brightly fluorescent FITC cells, by the cytometer software (FIG. 1/C-E) as done in prior art.
3b. Read the MFI values and MFI shifts for brightly fluorescent FITC cells (IgE positive cells) and brightly fluorescent PE cells (CD63 positive cells), respectively, calculated by the cytometer software. Calculate the Activation Indices by the formula as described in the present invention. Exemplary data are shown in FIG. 2 and Table 2.

1.5 Interpretation of Results

1. Analyze the percentage of CD63 positive cells as done with prior art methods and calculations, respectively. To obtain an optimal sensitivity and specificity, slightly different cut-off values should be applied for each allergen since:
   i) The negative controls show variable values, but usually below 5% CD63 activation.
   ii) Some allergens (e.g. food proteins and drug allergens) may cause non specific in vitro stimulation.
   iii) Some allergens (e.g. drugs) yield lower stimulation percentages in positive cases than e.g. inhalant protein allergens. Therefore, a lower cutoff value has to be chosen for low molecular weight drug allergens.
   As a rule, the cutoffs are determined by Receiver Operator Characteristic (ROC) curves enabling to achieve highest possible sensitivity by an optimal specificity. On the basis of extensive studies following cutoffs (positivity thresholds) are proposed:
   Inhalant and food allergens (protein mixes): ≥15%
   Hymenoptera venoms (proteins and protein mixes): ≥10%
   Drugs such as beta-lactam antibiotics and NSAIDs: ≥5% and SI≥2
   Drugs usually give lower CD63 activation percentages than other allergens. Therefore, a lower cut-off value should be taken, but the stimulation index (SI=allergen stimulation divided by the negative control) must be equal or superior to 2 in order to consider the result as positive.

Figure 4:
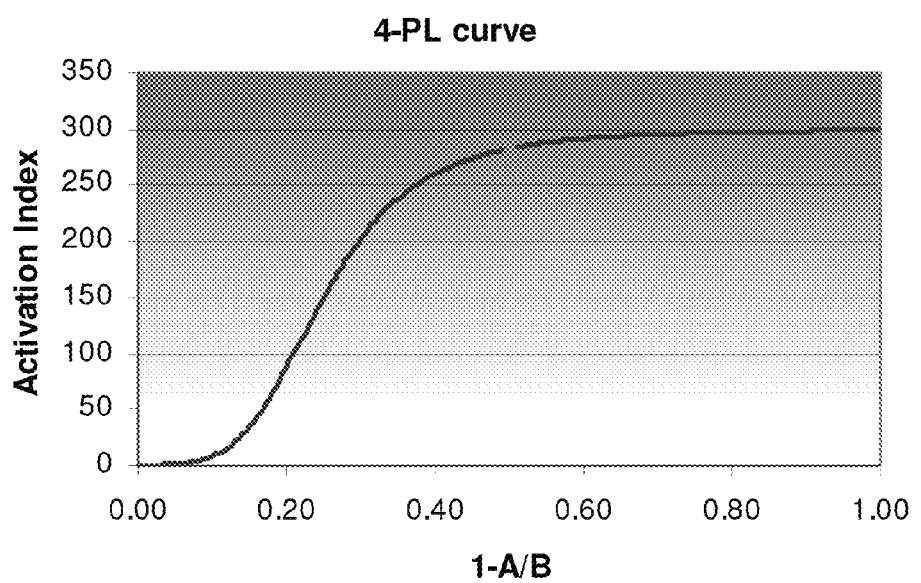
FIG. 4 shows an example of 4-PL curve using constant factors from Table 1.

2. Analyze the MFI shifts of IgE and/or CD63 mathematically transformed to the said Activation Indices as described in the present invention and as shown in Table 1 and FIG. 4. To obtain an optimal sensitivity and specificity, different cutoff values should be applied for different groups of allergens, since
   i) some allergens (e.g. food proteins, certain drug allergens) may cause non specific in vitro stimulation and
   ii) some allergens (particularly certain drug allergens) may yield lower stimulation percentages in positive cases than strong stimulators such as many protein allergens. Therefore, a lower cutoff value has to be chosen for most of the low molecular weight drug allergens.
   As a rule, the cutoffs are determined by Receiver Operator Characteristic (ROC) curves enabling to achieve highest possible sensitivity by an optimal specificity. On the basis of several studies (see Example 7) following preliminary cutoffs (positivity thresholds) are proposed:
   Hymenoptera venoms, inhalant and food allergens (proteins and protein mixes):
   Activation Index of >100
   Drugs such as beta-lactam antibiotics and NSAIDs:
   Activation Index of >6 and <30.

Protocol 2: CCR3-PE/CD63-FITC/IqE-AlexaFluor 647

2.1 Principle of the Assay

Whole blood samples are diluted and primed with Stimulation Buffer containing interleukin 3 (IL-3). Specific allergen is added and the cells are incubated to mimic the in vivo situation where, in IgE mediated allergies, specific IgE bound to the cellular surface via the high affinity IgE binding receptor (FcεRI) are bridged by the allergen and activate an intracellular enzymatic cascade leading to the activation of the basophils, but also so-called non-IgE mediated allergies, which are particularly observed with certain drugs, may lead to the same phenomenon on basophils. During this activation IgE bound to the basophils is internalized as well as intracellular vesicles containing the transmembrane protein CD63 are fused to the cellular membrane and, therefore, CD63 is exposed to the extracellular matrix.

A highly specific monoclonal antibody (mAb) recognizing the high affinity IgE binding receptor (FcεRI) is used as a positive control, leading to the activation of the basophils by mimicking the bridging event described above.

During the activation reaction, the Staining Reagent containing a mixture of monoclonal antibodies to human CCR3 labeled with phycoerythrin (anti-CCR3-PE) and to human CD63 labeled with fluorescein isothiocyanate (anti-CD63-FITC) is added. After stopping the reaction, the IgE Staining Reagent containing a monoclonal antibody to human IgE labeled with AlexaFluor 647 (anti-IgE-AlexaFluor 647) is added. The remaining erythrocytes are then removed by a lysing reaction and, after blocking this reaction, the cells are analyzed by flow cytometry.

2.2 Reagents

| | | |
|---|---|---|
| Stimulation Buffer Containing calcium, heparin and IL-3 | 1 vial lyoph. | Reconstitute with 50 ml of $H_2O$ |
| Stimulation Control anti-FcεRI mAb | 1 vial lyoph. | Reconstitute with 1.5 ml of Stimulation Buffer |
| Staining Reagent Mix of anti-CCR3-PE and anti-CD63-FITC mAb | 1 vial 2.2 ml | Ready to use |
| IgE Staining Reagent anti-IgE-AlexaFluor 647 | 1 vial 2.2 ml | Ready to use |
| Lysing Reagent 10x concentrated | 1 vial 25 ml | Dilute with 225 ml of deionized $H_2O$ |
| Wash Buffer stop of cell lysis | 1 vial 100 ml | Ready to use |
| Protein Allergen | 1 µl per vial | Dilute with 250 µl Stimulation Buffer |
| Low Molecular Weight (Drug) Allergen | lyoph. vial | Dilute with 250 µl Stimulation Buffer |

2.3 Assay Procedure

1. Mix the anti-coagulated blood sample by inverting the venipuncture tube several times.
2. Prepare fresh and pyrogen-free 3.5 ml polypropylene or polystyrene tubes.
3. For each patient, label pyrogen-free polystyrene tubes suited for Flow Cytometry measurements (e.g., PB=patient background=negative control; PC=stimulation control with anti-FcεR1 Ab; A1-1 for antigen 1 with dilution 1, A1-2 for allergen 1 with dilution 2, etc.)
4. Add 100 µl of Stimulation Buffer to each tube.
5. Pipet 50 µl patients whole blood to each tube. Be sure that the side wall and top of the tube is free of blood.
6. Mix gently.
7a. Pipet 50 µl of Stimulation Buffer (negative control) into the PB tube of each is patient.
7b. Pipet 50 µl of Stimulation Control into the PC tube of each patient.
7c. Pipet 50 µl of Allergen into the corresponding patient tubes.
8. Add 20 µl of Staining Reagent to each tube.
9. Mix gently, cover the tubes and incubate for 15 minutes at 37° C. in a water bath (using an incubator will take about 10 minutes longer incubation time due weaker heat transfer).
10. Stop the reaction by putting the tubes into an ice bath.
11. Add 20 µl of IgE Staining Reagent to each tube.
12. Mix gently, cover the tubes and incubate for 10 minutes at 2-8° C. in the dark.
13. Vortex gently the sedimented cells.
14. Add 2 ml pre-warmed (18-28° C.) Lysing Reagent to each tube.
15. Incubate for 5-10 minutes at 18-28° C.
16. Centrifuge the tubes for 5 minutes at 500×g.
17. Decant the supernatant by inverting the tubes and drying the drops which may remain at the edge of the tubes using a blotting paper.
18. Resuspend the cell pellet with 500 µl of Wash Buffer.
19. Vortex gently.
20. Proceed to flow cytometry within 2 hours.
21. If not analysed within 2 hours, processed samples must be stored at 2-8° C., protected from light, and analysed within 8 hours.

2.4 Flow Cytometry

Flow cytometric analysis can be performed on any flow cytometer containing a 488 nm argon laser (blue-green excitation light) with a 633 nm red laser diode and the corresponding software. The flow cytometer must be equipped to detect Forward Scatter, Side Scatter and the three fluorochromes FITC, PE and AlexaFluor 647 (or alternatively APC).

At least 150 basophilic cells must be analyzed, requiring a total amount of 50,000 to 80,000 leukocytes to analyze. Because of the lower activation percentage in drug allergies, the lower limit of basophilic cells to be analyzed should be set to 200 or more.

Figure 3:
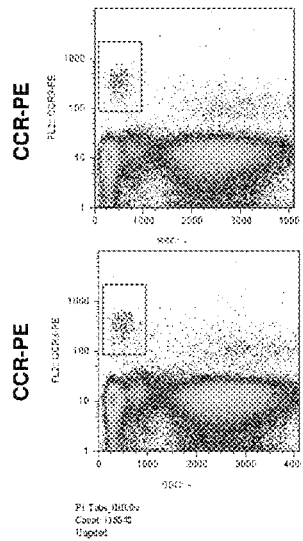
FIG. 3 shows a three step analytical procedure.
Figure 3:
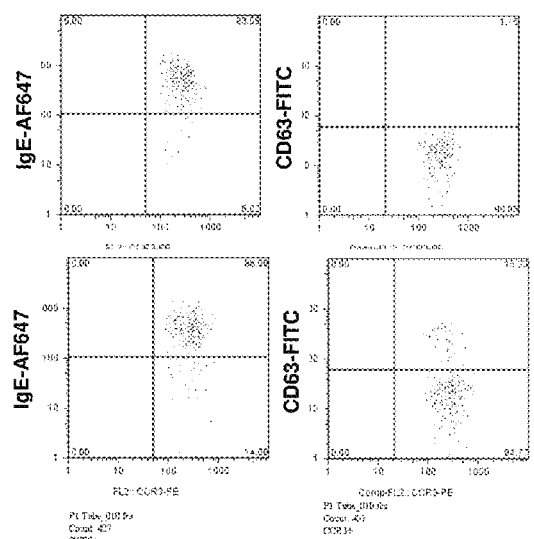

The analysis is based on two steps (see FIG. 3):

1. Set a gate 1 (R1) by including the entire basophil population $CCR3^{pos}$ with low Side Scatter SSC (FIG. 3/A).
2a. Calculate the percentage of CD63 positive cells (brightly fluorescent FITC; Q2) compared to the total amount of basophilic cells gated in R1 as done in prior art (FIG. 3/C).
2b. Read the MFI values and MFI shifts for brightly fluorescent FITC cells (CD63 positive cells; FIG. 3/C) and brightly fluorescent AlexaFluor 647 cells (IgE positive cells; FIG. 3B), respectively, calcaluted by the cytometer software. Exemplary data are shown for the negative control (Stimulation Buffer) and the positive Stimulation Control. Calculate the Activation Indices by the formula as described in the present invention and as shown in Table 1 and FIG. 4.

2.5 Interpretation of Results

1. Analyze the percentage of CD63 positive cells as done with prior art methods and calculations, respectively. To obtain an optimal sensitivity and specificity, slightly different cutoff values should be applied for each allergen since:
   i) The negative controls show variable values, but usually below 5% CD63 activation.
   ii) Some allergens (e.g. food proteins and drug allergens) may cause non specific in vitro stimulation.
   iii) Some allergens (e.g. drugs) yield lower stimulation percentages in positive cases than e.g. inhalant protein allergens. Therefore, a lower cutoff value has to be chosen for low molecular weight drug allergens.
   As a rule, the cutoffs are determined by Receiver Operator Characteristic (ROC) curves enabling to achieve highest possible sensitivity by an optimal specificity. On the basis of extensive studies following cutoffs (positivity thresholds) are proposed:
   Inhalant and food allergens (protein mixes): ≥20%
   Hymenoptera venoms (proteins and protein mixes): ≥15%
   Drugs such as beta-lactam antibiotics and NSAIDs: ≥5% and SI≥2
   Drugs usually give lower CD63 activation percentages than other allergens. Therefore, a lower cutoff value should be taken, but the stimulation index (SI=allergen stimulation divided by the negative control) must be equal or superior to 2 in order to consider the result as positive.
2. Analyze the MFI shifts of IgE and/or CD63 mathematically transformed to the said Activation Indices as described in the present invention and as shown in Table 1 and FIG. 4. To obtain an optimal sensitivity and specificity, different cutoff values should be applied for different groups of allergens, since
   i) some allergens (e.g. food proteins, certain drug allergens) may cause non specific in vitro stimulation and
   ii) some allergens (particularly certain drug allergens) may yield lower stimulation percentages in positive cases than strong stimulators such as many protein allergens. Therefore, a lower cutoff value has to be chosen for most of the low molecular weight drug allergens.
   As a rule, the cutoffs are determined by Receiver Operator Characteristic (ROC) curves enabling to achieve highest possible sensitivity by an optimal specificity. On the basis of several studies (see Example 7) following preliminary cutoffs (positivity thresholds) are proposed:
Hymenoptera venoms, inhalant and food allergens (proteins and protein mixes):
Activation Index of >100
Drugs such as beta-lactam antibiotics and NSAIDs:
Activation Index of >6 and <30.

The following illustrative examples show the technical benefits of the invented method(s) according to the invention over prior art methods without being understood as limiting the scope of the invention.

Example 1

EDTA vs. Heparin vs. ACD (Citrate) Blood

Blood from healthy blood donors or allergic patients was drawn into three different venipuncture tubes containing as anticoagulant either EDTA or Heparin or Citrate (ACD).

Figure 5A:
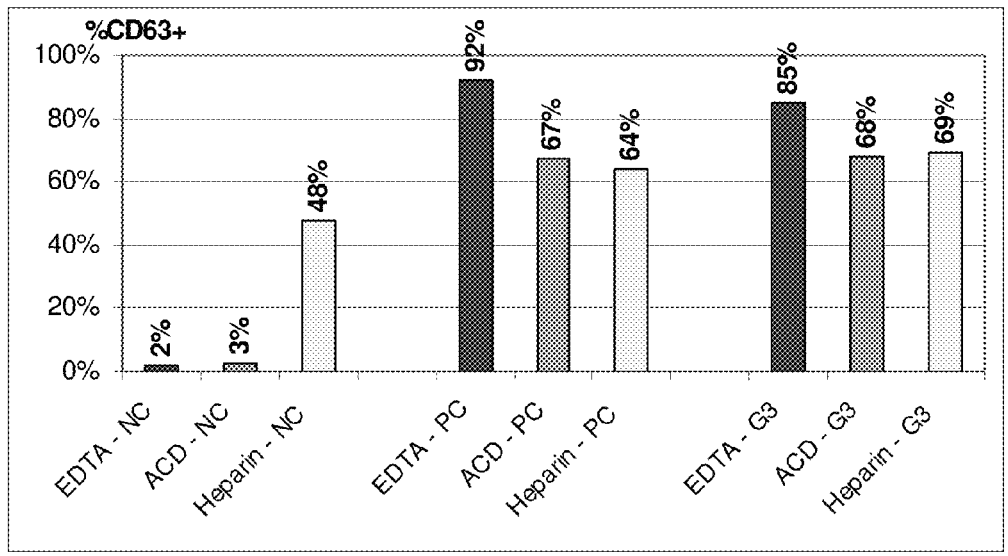
FIG. 5A shows a direct comparison of the three different blood preparations from a orchard grass (G3) allergic patient.
Figure 5B:
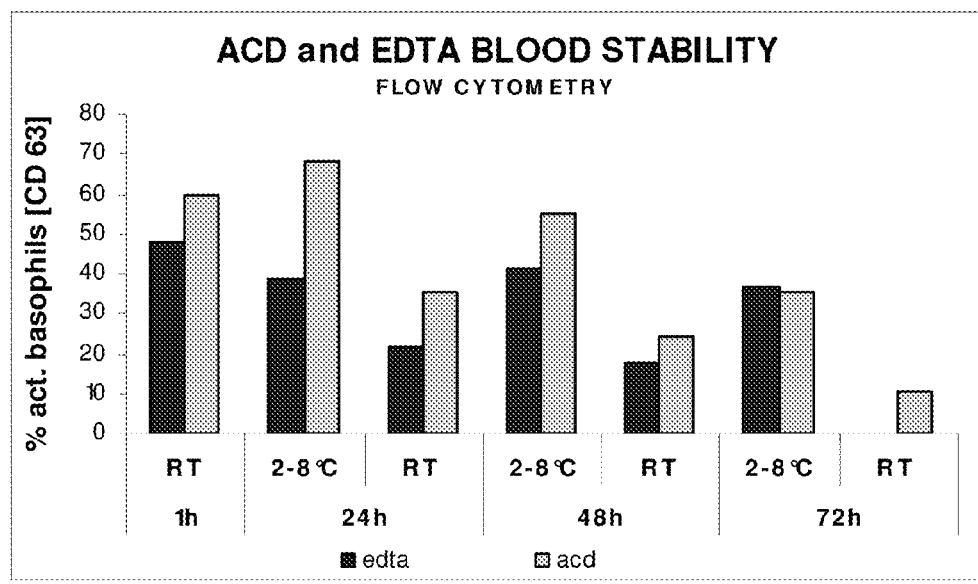
FIG. 5B shows results of the test for stability and reactivity of basophils stored in EDTA or ACD blood.
Figure 5C:
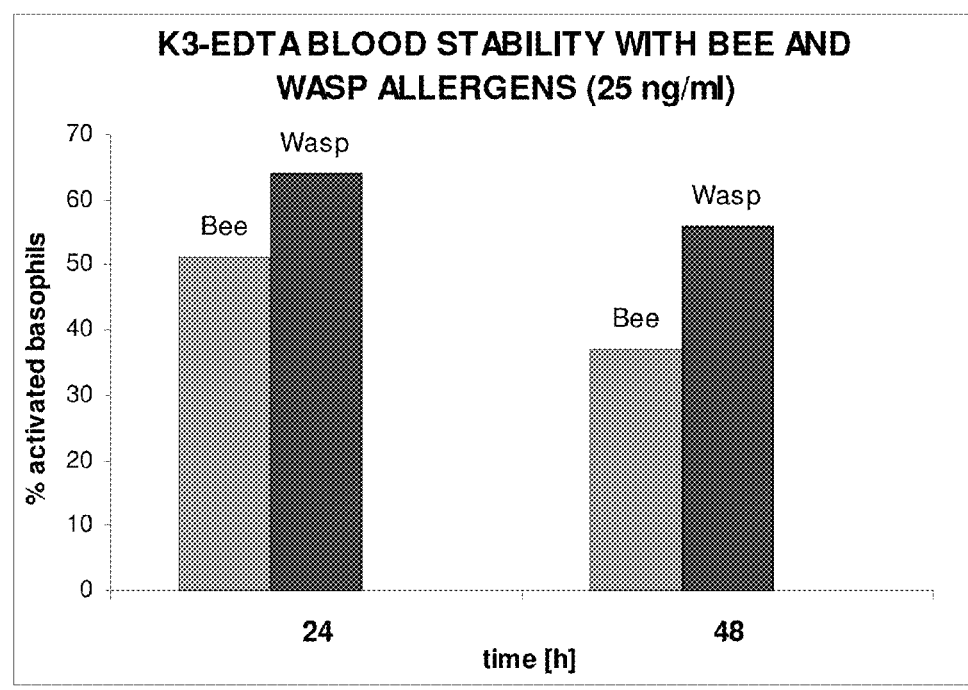
FIG. 5C shows mean stimulation values after 24- and 48-hour storage.

All blood samples were analysed according to Protocol 1 and stimulated with Stimulation Buffer (negative control=NC), anti-FcεRI mAb (positive Stimulation Control=PC) and with allergens as specified in FIGS. 5A, 5C and 5D. The results are expressed in percentage of CD63 expression.

A direct comparison of the three different blood preparations from a orchard grass (G3) allergic patient is shown in FIG. 5A. Heparin seems to unspecifically stimulate NC which is observed from time to time in other cases as well, whereas this is not seen here and is also not reported in other cases for ACD or EDTA blood, PC and G3 (50 ng/ml) are clearly positive with all blood samples, however EDTA samples give slightly higher stimulation reactions.

EDTA, ACD or Heparin venipuncture tubes were stored either at 2-8° C. or at room temperature (RT) for different time points (1, 24, 48 and 72 hours) and then centrifuged. In the case of Heparin, the blood separation did only work after storage of less than 24 hours. For EDTA and ACD, the blood separation worked well even after 72 hours storage time, however better after 2-8° C. than room temperature storage. The stability and reactivity of basophils stored in EDTA or ACD blood was tested according to Protocol 1. The results are summarized in FIG. 5B.

In the last experiment, EDTA blood from 6 bee and 9 wasp allergic patients was stored for 24 and 48 hours and subsequently stimulated with bee or wasp venom extract (25 ng/ml each) according to Protocol 1. The mean stimulation values after 24- and 48-hour storage are shown in FIG. 5C. All 6 bee and all 9 wasp allergic patients gave values above the cutoff (positivity threshold) of 10% CD63 activation, clearly showing that basophils are functionally active for at least 48 hours when kept in EDTA blood at 2-8° C.

It can be concluded that only basophils stored in EDTA blood at 2-8° C. allow to analyze blood samples after a storage period of longer than 48 hours, but not in Heparin blood as used in most prior art methods. ACD blood may also be used after longer storage times, however the results are less consistent than with EDTA blood and sometimes elevated background (NC) values can be observed. Therefore, only the protocols presented by this invention allow to send blood samples out to a specialized testing laboratory which is located far away from the site (e.g the doctor's office or a local hospital) where patient blood is collected.

Example 2

Diluted vs. Purified (Washed) Blood Cells

The cellular reactivity depends very much on the conditioning of the blood cells before stimulation, i.e. the matrix for the stimulation reaction is very crucial. It must contain heparin, calcium and, preferably, IL-3 (except for specific applications such as the follow up of insect venom immunotherapy), but plasma factors may influence the reactivity of blood basophils, too.

Therefore, we established two protocols, one with diluted whole blood, wherein the EDTA blood sample is diluted 1 in 4 with cellular incubation buffer (the Stimulation Buffer) and another with purified blood, wherein the basophils were transferred from its plasma matrix to a plasma-free matrix such as the cellular incubation buffer by centrifuging and washing the blood cells. The following illustrative examples show the dramatic influences which the cellular preparation method may have on the reactivity of patients' blood cells in different clinical settings.

Figure 6:
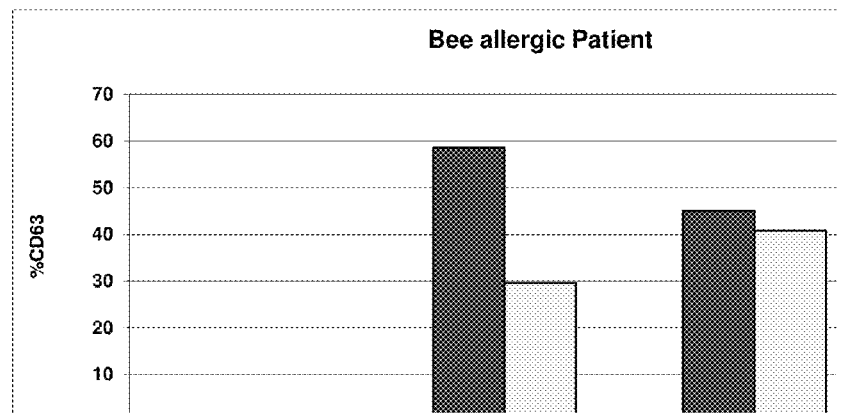
FIG. 6 shows reactions in one bee allergic (panel A) and two wasp allergic patients (panels B and C) to the corresponding allergen stimulus in three different concentrations (c1: 1 µg/ml, c2: 0.3 µg/ml, c3: 0.1 µg/ml of bee or wasp venom extract).
Figure 6:
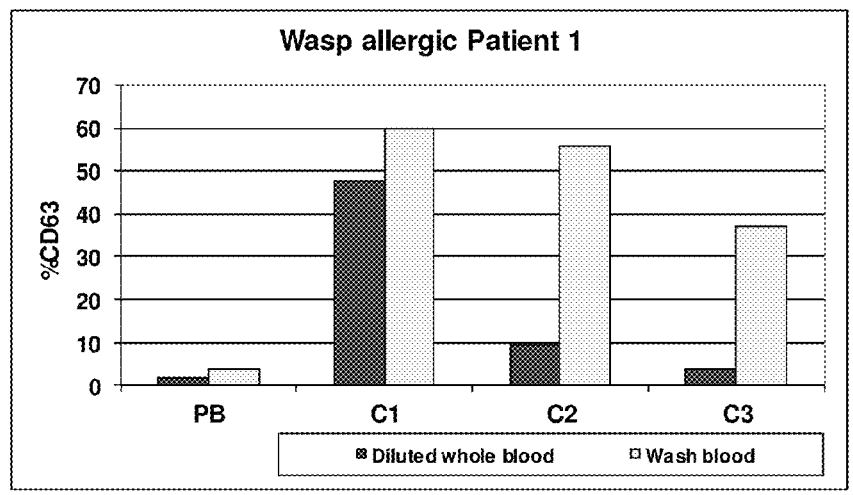
Figure 6:
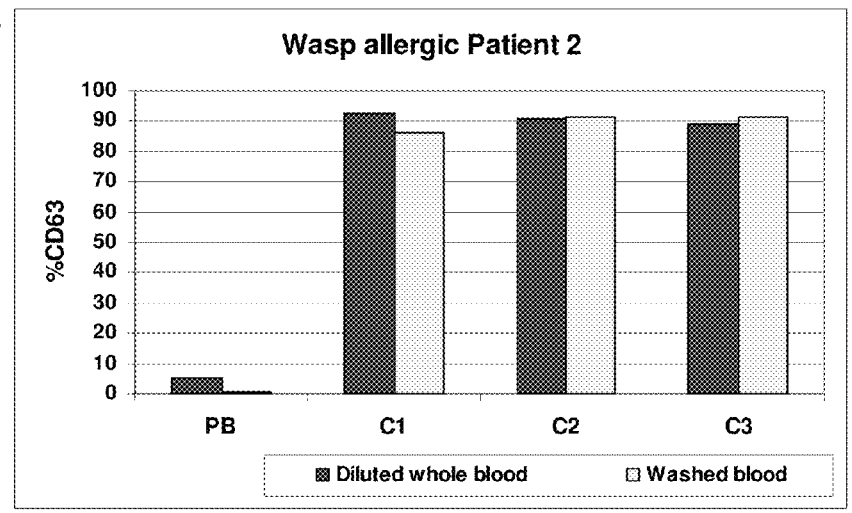

In FIG. 6, one bee allergic and two wasp allergic patients were reacting totally different to the corresponding allergen stimulus in three different concentrations (c1: 1 μg/ml, c2: 0.3 μg/ml, c3: 0.1 μg/ml of bee or wasp venom extract). In one case the diluted blood method is optimal, in one case the purified blood cells work best, in a third case both methods give about the same stimulation yield.

Figure 7A:
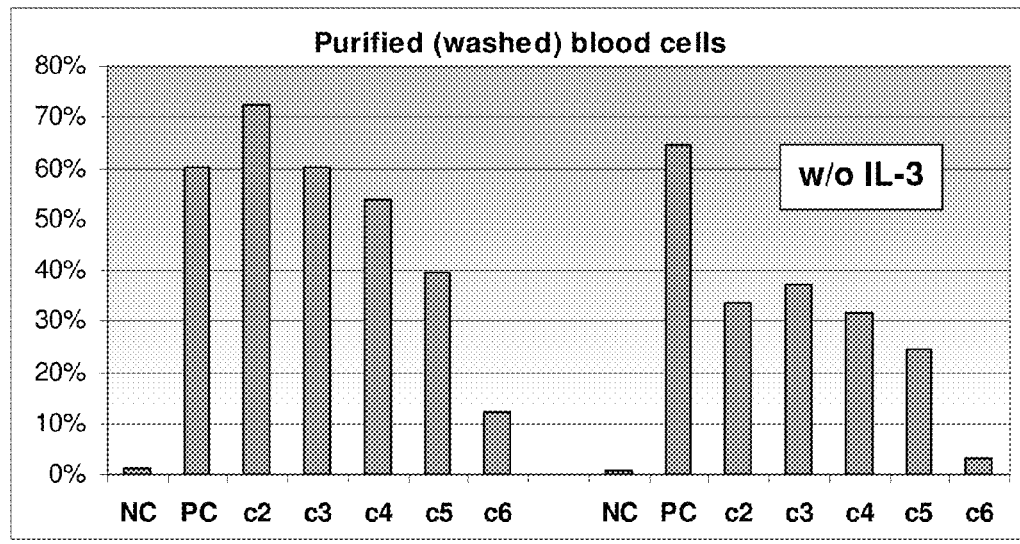
FIG. 7 shows tests with bee allergic patient. It can clearly be seen that both the diluted whole blood and the washed blood protocol give the same qualitative, but different quantitative results.
FIG. 7B shows reaction of basophils from the same patient, but in diluted whole blood.
Figure 7B:
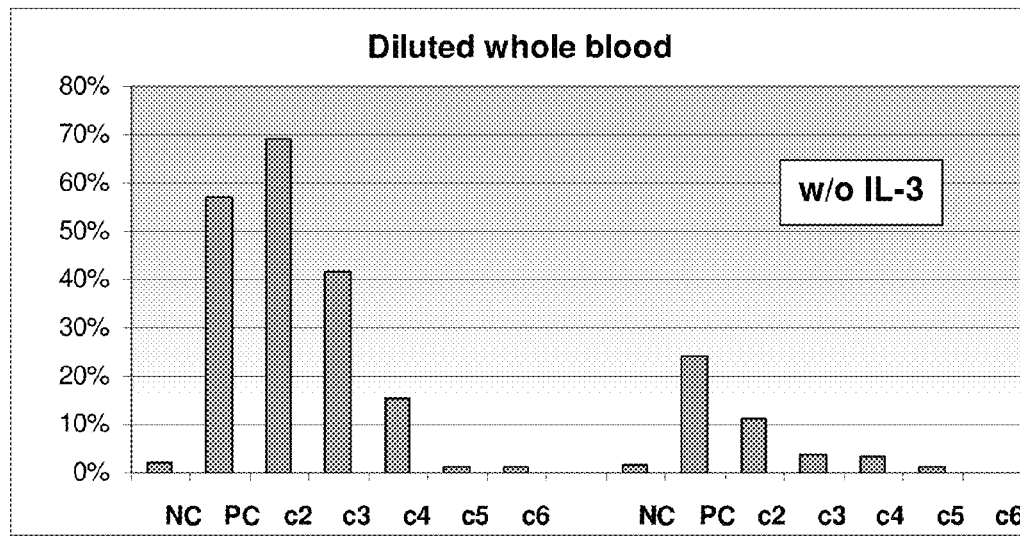

It depends now on the purpose of the test and, even more important, on the allergen concentration employed which method should optimally be used. From FIG. 7 representing a bee allergic patient, it can clearly be seen that both the diluted whole blood and the washed blood protocol give the same qualitative, but different quantitative results, in most cases strictly dependent on the allergen concentration used (c2 equals 3125 ng/ml bee venom extract; c3: 625 ng/ml; c4: 125 ng/ml; c5: 25 ng/ml; c6: 5 ng/ml). The basophils from washed blood are reacting to a 25-fold lower concentration of bee venom extract (FIG. 7A, left panel) than the basophils from the same patient, but in diluted whole blood (FIG. 7B, left panel).

Figure 8A:
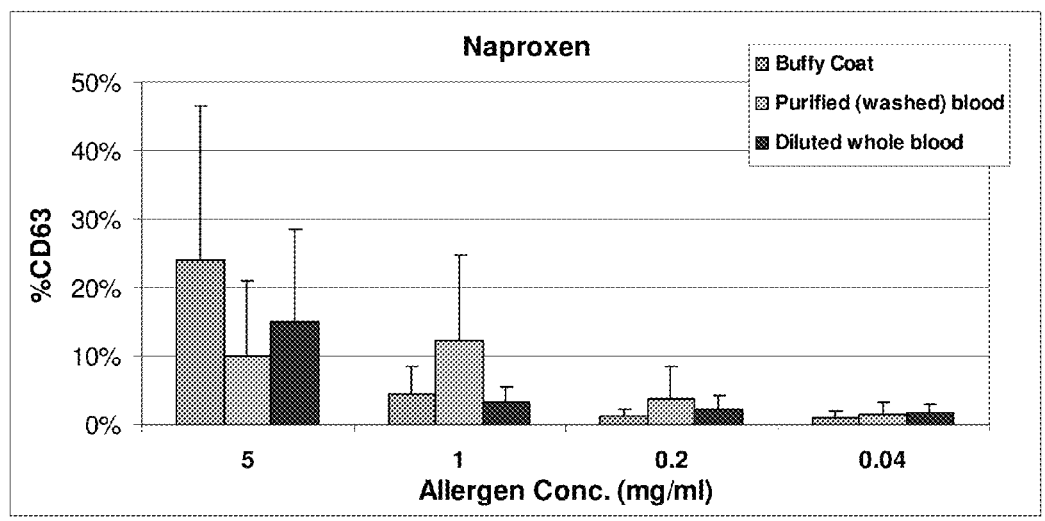
FIG. 8A shows that 5 mg/ml of Naproxen leads to cytotoxic effects which can be observed with all blood preparation methods.
Figure 8B:
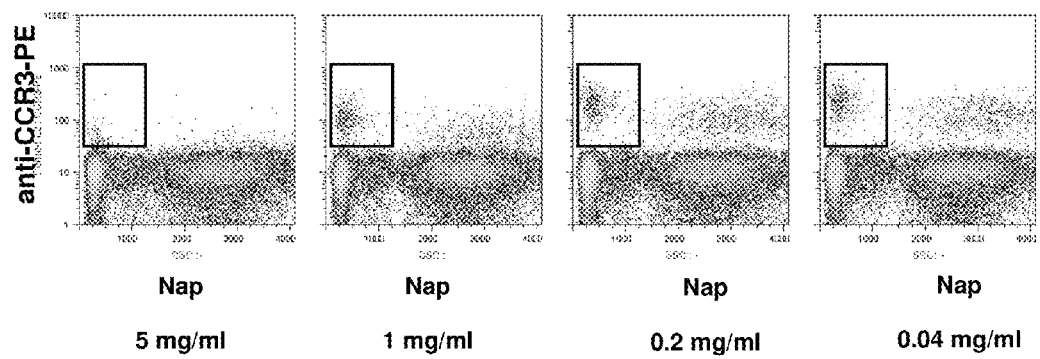
FIG. 8B shows results of experiments with diluted whole blood method together with stimulation Protocol 2.

High or, more precise, too high allergen concentrations can lead to unspecific stimulation of or even cytotoxic effects on blood basophils. As it can be seen in FIG. 8A, these effects are again dependent from the preparation and conditioning of the blood cells. The results are presented as the means+1 standard deviation from 21 normal blood donors tested with 4 different concentrations of Naproxen. The washed blood cells are more susceptible for unspecific stimulatory effects of higher allergen concentrations as observed for 1 mg/ml of Naproxen. The concentration of 5 mg/ml of Naproxen leads to cytotoxic effects which can be observed with all blood preparation methods (FIG. 8A). This cytotoxic effect is further illustrated in FIG. 8B using the diluted whole blood method together with stimulation Protocol 2. The CCR3 positive cell population has disappeared after stimulating the blood cells with 5 mg/ml of so Naproxen, but not with concentrations mg/ml, clearly showing that the basophils are physically not intact anymore.

To summarize, the use of diluted whole blood is recommended since the basophil stimulation with test substances (allergens) is more reproducible and drug allergens lead to less unspecific and/or toxic effects on basophils. On the other hand, the purified blood cells are useful when following specific immunotherapy (see also Example 12) where remaining plasma factors may interfere with the cell stimulation reaction. Another advantage of using washed blood is the rapid and automatizable processing of blood samples by ommitting the time- and reagent-consuming process of erythrocyte lysis before analyzing the basophils on the flow cytometer.

Example 3

Lysis Procedure

As just mentioned above, the removal of erythrocytes before analyzing the basophils on a flow cytometer is a prerequisite to correctly gate in resting vs. activated basophils and to get highly informative and quantitative results. In prior art methods, this is, beside the cell stimulation part, the most delicate and most time-consuming step in the entire analysis of quantitative basophil stimulation.

Figure 9A:
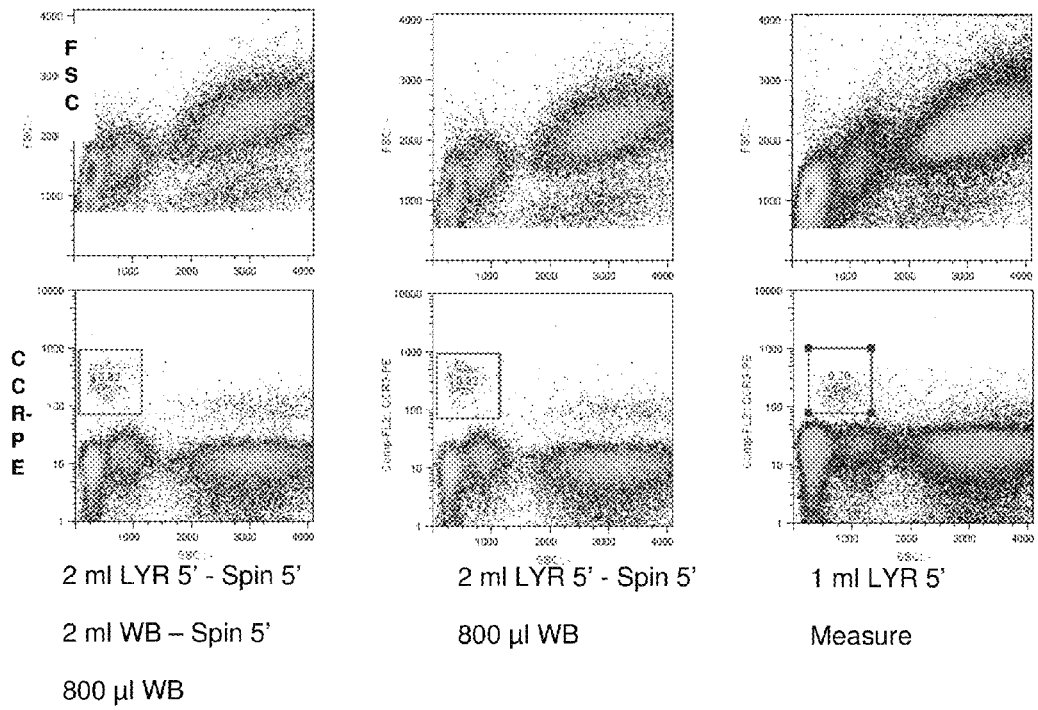
FIG. 9A shows the detection and gating of basophils using the CCR3-PE selection marker.
Figure 9B:
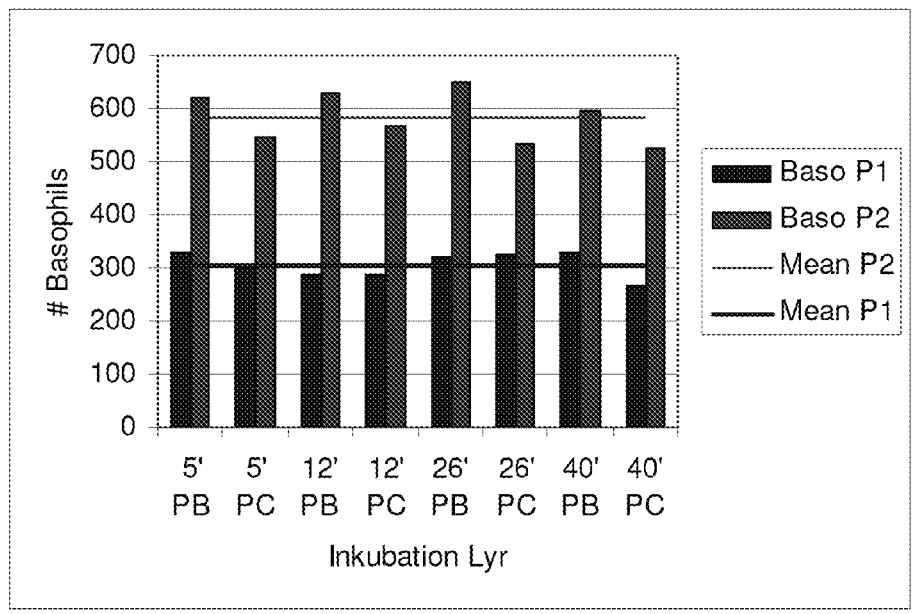
FIG. 9B shows the exemplary basophil recoveries after stimulation with negative control (PB) or positive Stimulation Control (PC) for two blood donors.

With the invented stimulation Protocol 2 combined with the CCR3 basophil selection marker it is possible to simplify and speed up or even automatize this process. In FIG. 9A, the detection and gating of basophils using the CCR3-PE selection marker is shown. From the left to the right panel, different erythrocyte lysing procedures are tested (LYR=Lysing Reagent; WB=Wash Buffer). The left panel shows a procedure as used in prior art methods including two centrifugation and one washing steps, the right panel clearly shows that neither a washing nor a centrifugation step is necessary to receive a clear-cut separation of basophils from the other cells by lysing the erythrocytes for 5 minutes and directly injecting this cell suspension into the flow cytometer. The smoothness and reproducibilty of the lysis procedure as shown in the right panel of FIG. 9A, is further supported by the fact that basophil recovery, after the cell suspension is subjected to treatment with the Lysing Reagent (Lyr), is stable for at least 40 minutes. Exemplary basophil recoveries after stimulation with negative control (PB) or positive Stimulation Control (PC) are shown for two blood donors (FIG. 9B).

Example 4

Influence of IL-3

Early studies with other basophil activation tests such as histamine release test and, particularly, the sulfidoleukotriene release test (CAST-ELISA) have shown that priming of basophils with interleukin 3 (IL-3) leads to a higher and more stable release of this basophil activation mediators (Y. Kurimoto, A L. de Week, C. A. Dahinden: The effect of interleukin 3 upon IgE-dependent and IgE-independent basophil degranulation and leukotriene generation. Eur J Immunol 1991, 21, 361-368). We have studied the activation of basophils dependent on 0.2 to 200 ng/ml of IL-3 (final dilution) by following the CD63 expression marker is using Protocol 1. The optimum stimulation was reached at a concentration of 2 ng/ml, but it also works quite well with 0.2, 20 or 200 ng/ml (data not shown). However, as it can be seen in FIGS. 7A and 7B (right panels) the presence of IL-3 is mandatory for a significant stimulation of basophils with allergens, independent whether washed blood (FIG. 7A) or diluted whole blood (FIG. 7B) is used. On the left panels the stimulation with 5 different concentrations of bee venom extract (c2 equals 3125 ng/ml of bee venom extract; c3: 625 ng/ml; c4: 125 ng/ml; c5: 25 ng/ml; c6: 5 ng/ml) in the presence of 2 ng/ml of IL-3 is shown, on the right panels the same stimulations, but without IL-3, are represented.

The following illustrative and comparative example shows the benefit of using the invented method(s) over prior art methods in maximizing the cellular responses of insect venom allergic patients during the follow-up of venom immunotherapy (VIT).

Example 5

Comparative Results During VIT (Bee and Wasp)

The theory behind the bee and wasp VIT is that the patient's cellular reactivity should be reduced to an amount which is not anymore dangerous for a patient, i.e. which does not anymore lead to a systemic (anaphylactic) reaction when a patient would be re-stung by the respective hymenoptera. This decreased cellular reactivity may be reflected by a decreased or negative expression of the CD63 basophil activation marker. Therefore, the goal would be that a patient protected from an anaphylactic reaction could be differentiated by a negative CD63 expression index from a patient who would not be protected after the VIT.

Figure 17:
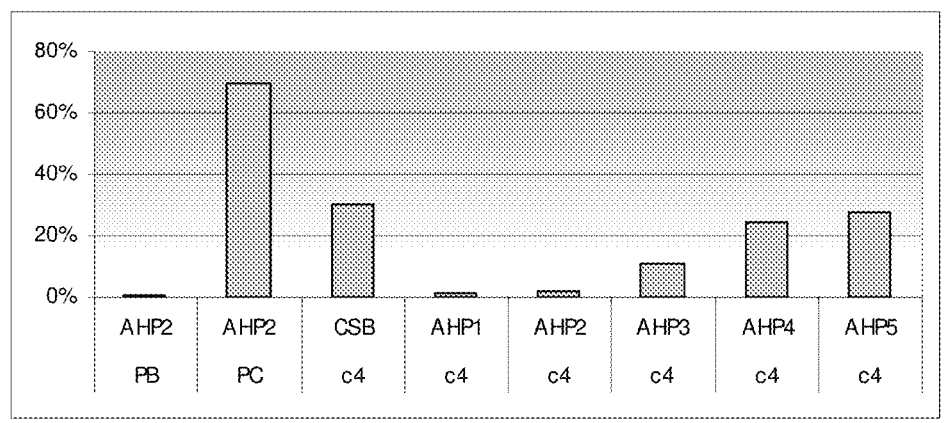
FIG. 17 shows results of Example 5 (comparative results during VIT (Bee and Wasp)). The effect of the addition of autologous plasma (AHP) to purified blood of a bee venom allergic patient after 5 years of VIT is shown.

Here we represent an example of a bee allergic patient who was under bee VIT for approximately five years and did not react anymore to an in vivo sting challenge by a living bee, i.e. the patient is regarded as symptom-free and protected from another systemic or anaphylactic due to a bee sting. As it can be seen from FIGS. 7A and 7B (left panels) the presence of IL-3 is mandatory for a significant stimulation of basophils from this recovered bee allergic patient, independent whether washed blood (FIG. 7A) or diluted whole blood (FIG. 7B) is used. It can be clearly seen that the above theory did not lead to the desired result. However, when the incomplete basophil stimulator or basophil priming reagent, the IL-3, is ommitted (FIGS. 7A and 7B; right panels) in the diluted whole blood protocol, the basophils can not be stimulated anymore over the positivity threshold of 15% CD63 expression, i.e. indicating that the theory stipulated above may work. On the left panels of FIGS. 7A and 7B the stimulation with 5 different concentrations of bee venom extract (c2 equals 3125 ng/ml of bee venom extract; c3: 625 ng/ml; c4: 125 ng/ml; c5: 25 ng/ml; c6: 5 ng/ml) in the presence of 2 ng/ml of IL-3 is shown, on the right panels the same stimulations, but without IL-3, are represented. To our surprise, this works with whole blood only (FIG. 7B), but not with purified blood basophils (FIG. 7A). This must most probably be due to protecting plasma factors present in the whole blood protocol. When autologous plasma from the same recovered and protected bee allergic patient is added to the purified blood basophils, the protecting effect, i.e. the absence of a significant basophil stimulation as proven by the reduced CD63 expression, can also be observed in the purified blood protocol (see FIG. 17). The presence of 25% (AHP1), 12.5% (AHP2) and 6.3% of autologous plasma (AHP3) reduces the CD63 expression significantly at an allergen concentration of 125 ng/ml bee venom extract (c4) when compared to the control sample in pure cellular stimulation buffer (CSB). Negative Control (PB) as well as positive Stimulation Control (PC) is not influenced by the presence of 12.5% of autologous plasma.

Therefore, the management of bee and wasp allergic patients under VIT and the potential prediction of the outcome of such a VIT may be followed by the correct application and interpretation of whole blood and purified blood protocols in the presence and absence of IL-3, respectively.

Example 6

Advantages of Using CCR3 as Selection Marker as Compared to IgE

Figure 10A:
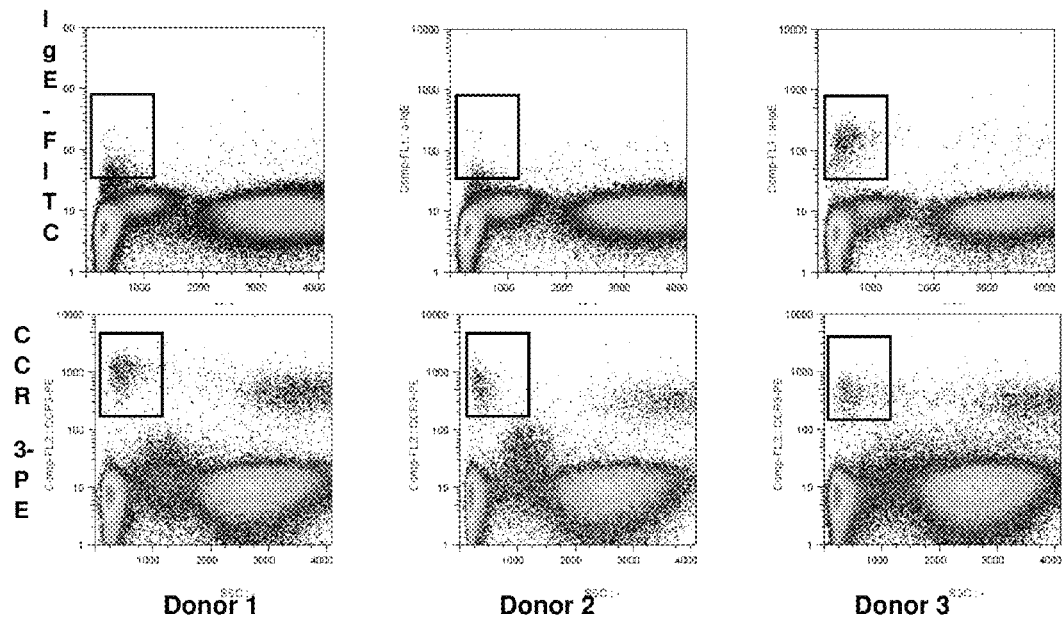
FIG. 10A shows that the basophils are much better separated from the other cells when using CCR3 as selection marker (lower panels).

In Protocol 1 anti-IgE-FITC is used as the basophil selection marker, whereas in Protocol 2 anti-CCR3-PE is used. FIG. 10A clearly shows that the basophils are much better separated from the other cells when using CCR3 as selection marker (lower panels). Particularly when basophilic cells are stimulated (e.g. with the positive Stimulation Control, the anti-FcεRI mAb) it can happen that the IgE positive basophilic cells are shifting due to an activation of the IgE marker which results in a downregulation of the IgE MFI. This can be observed for blood donor 1 and, particularly, for donor 2 (FIG. 10A, upper panels). The CCR3 marker is much more stable, even on highly stimulated basophils.

Figure 10B:
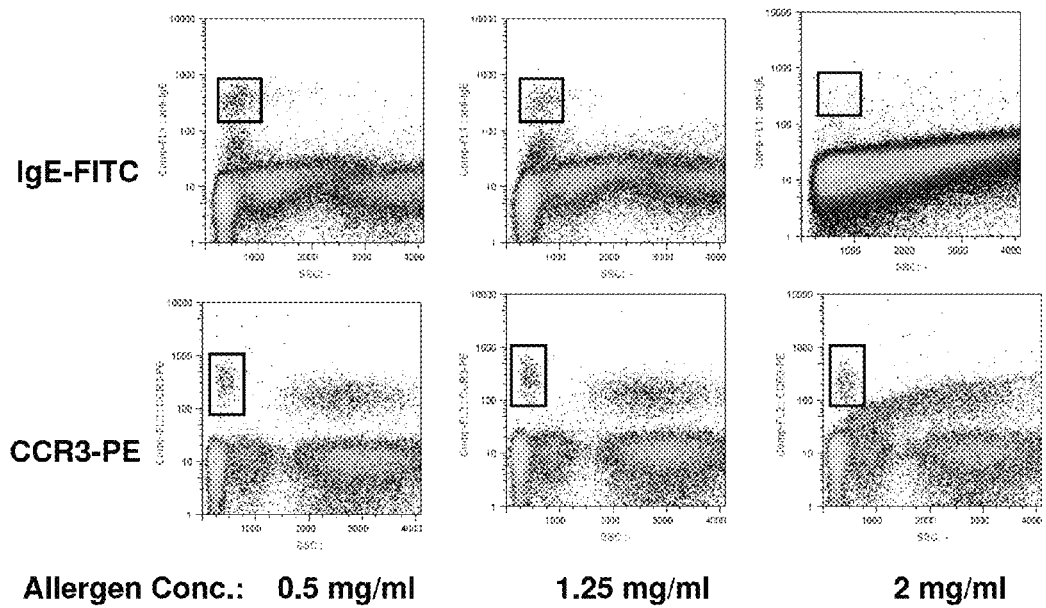
FIG. 10B shows a similar phenomenon when basophilic cells are stimulated with drug allergens such as amoxicillin, particularly when high allergen concentrations are applied.

A similar phenomenon can be observed when basophilic cells are stimulated with drug allergens such as Amoxicillin, particularly when high allergen concentrations are applied (see FIG. 10B). IgE positive basophilic cells are disappearing when stimulated with 2 mg/ml Amoxicillin (FIG. 10B; upper right panel); CCR3 positive cells can still be easily identified.

Figure 10C:
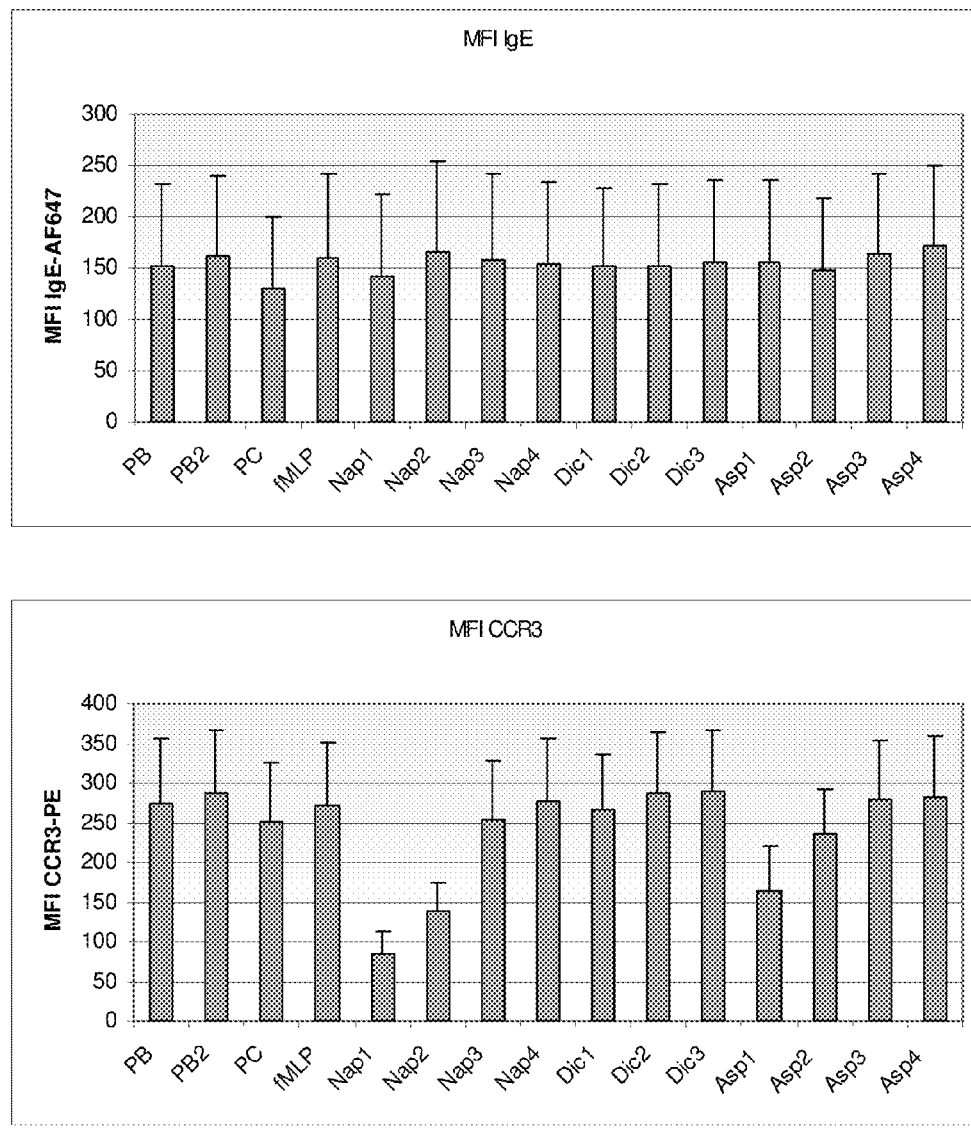
FIG. 10C shows that in contrast to the IgE selection marker (IgE-AF647; upper panel), high concentrations of Naproxen (Nap1, 5 mg/ml, and Nap2, 1 mg/ml) and Aspirin (Asp1, 5 mg/ml), respectively, known to be cytotoxic for basophilic cells, a down-regulation of MFI-CCR3 (lower panel) is observed.

Another advantage of using CCR3 as basophil selection marker is in the discrimination between specific basophil activation and unspecific or cytotoxic effects of high drug allergen concentrations on basophils. In contrast to the IgE selection marker (IgE-AF647; FIG. 10C, upper panel), high concentrations of Naproxen (Nap1, 5 mg/ml, and Nap2, 1 mg/ml) and Aspirin (Asp1, 5 mg/ml), respectively, known to be cytotoxic for basophilic cells show a clearcut downregulation of MFI-CCR3 (FIG. 10C, lower panel). This effect is visible with the anti-CCR3 selection marker only. This CCR3 MFI shift correlates well with unspecific stimulation of or toxic effects on basophils. In other words, the CCR3 selection marker can also be used to distinguish between cytotoxic and non-toxic concentrations of (drug) allergens and, therefore, CCR3 helps in optimizing the allergen concentrations being used in clinical settings of the invented methods.

To summarize, the IgE density on human basophil membrane, i.e. represented by the MFI, is highly variable from one patient to another patient and also strongly influenced by the stimulation reaction per se (see FIG. 10A) as well as by high drug allergen concentrations (see FIG. 10B). The benefit of using another selection marker such as CCR3 or CD13 is to standardize the basophil selection by a marker which is constitutively expressed on basophil membranes additionally showing a limited variation in membrane density from patient to patient. Another benefit of using the anti-CCR3 antibody is in the selection of a cellular population comprising nearly 100% of basophils in contrast to the anti-IgE, where only 85-95% of basophils with an additional contamination with monocytes and dendritic cells are selected. A third benefit of using CCR3 or CD13 is the absence of potential interferences with anti-IgE or anti-FcεRI mAbs used as the positive Stimulation Controls. A fourth benefit of using CCR3 or CD13 is in the absence of circulating CD13 or CCR3 antigens, in contrast to the use of anti-IgE where, particularly in the diluted whole blood protocol, huge variations in circulating IgE molecules may interfere or even inhibit basophil staining with anti-IgE-FITC.

The following illustrative example shows the interchangeability between IgE and $F_c\epsilon RI$ for basophil selection as well as for basophil activation.

Example 7

Alternative Use of $F_c\epsilon RI$ Instead of IgE

Figure 11A:
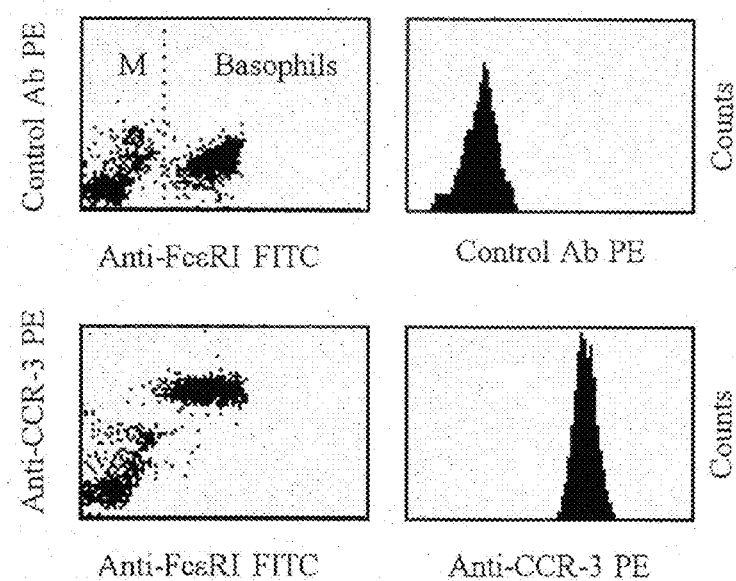
FIG. 11A shows that anti-FcεRI-FITC clearly separates the basophils from other blood cells (upper panels) and that the FcεRI positive cells are also CCR3 positive which clearly indicates that only basophilic cells are labeled and, therefore, selected by the anti-FcεRI mAb (lower panels).
Figure 11B:
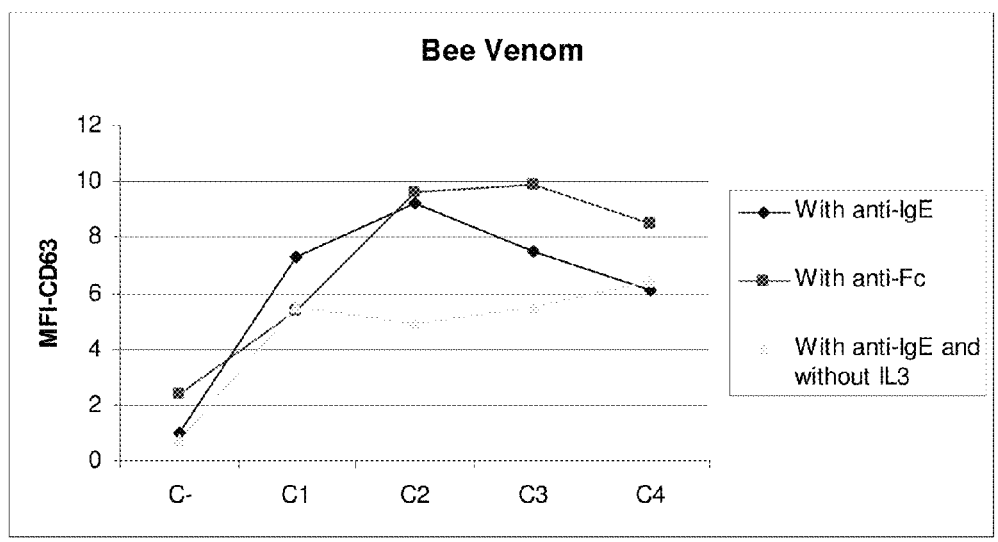
FIG. 11B shows that both the anti-IgE and the anti-FcεRI can be used for basophil selection, as indicated by the upregulation of the MFI-CD63, in a bee allergic patient.

Anti-IgE can be replaced by anti-$F_c\epsilon RI$ for basophil selection as well as for basophil activation. In FIG. 11A (upper panels) it can be seen that anti-$F_c\epsilon RI$-FITC clearly separates the basophils from other blood cells. From the lower panels of FIG. 11A it can be concluded that the $F_c\epsilon RI$ positive cells are also CCR3 positive which clearly indicates that only basophilic cells are labelled and, therefore, selected by the anti-$F_c\epsilon RI$ mAb. Consequently, in a bee allergic patient it could be shown that both the anti-IgE and the anti-$F_c\epsilon RI$ can be used for basophil selection as indicated is by the upregulation of the MFI-CD63 (FIG. 11B). C-represents the negative control (Stimulation Buffer only), while C1, C2, C3 and C4 represent the stimulation with 1, 0.3, 0.1 and 0.03 µg/ml of bee venom extract.

Figure 11C:
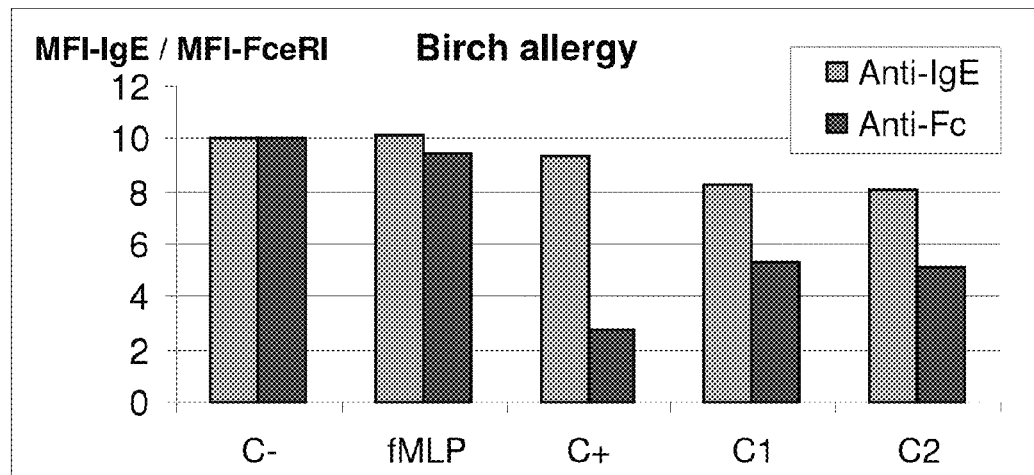
FIG. 11C shows that downregulation of the MFI-FcεRI was even more pronounced than the MFI-IgE in a birch pollen allergic patient.

In a birch pollen allergic patient it could be shown that downregulation of the MFI-$F_c\epsilon RI$ was even more pronounced than the MFI-IgE (FIG. 11C) indicating a strong activation with the Stimulation Control (C+), 1 µg/ml (C1) and 0.2 µg/ml (C2) of birch pollen extract. For better comparing the results, the MFIs of the negative control (C−) were set to 10 for both markers and the rest of the data were normalized correspondingly. fMLP is an alternative positive control which usually gives lower stimulation yields than anti-$F_c\epsilon RI$ mAb.

Figure 11D:
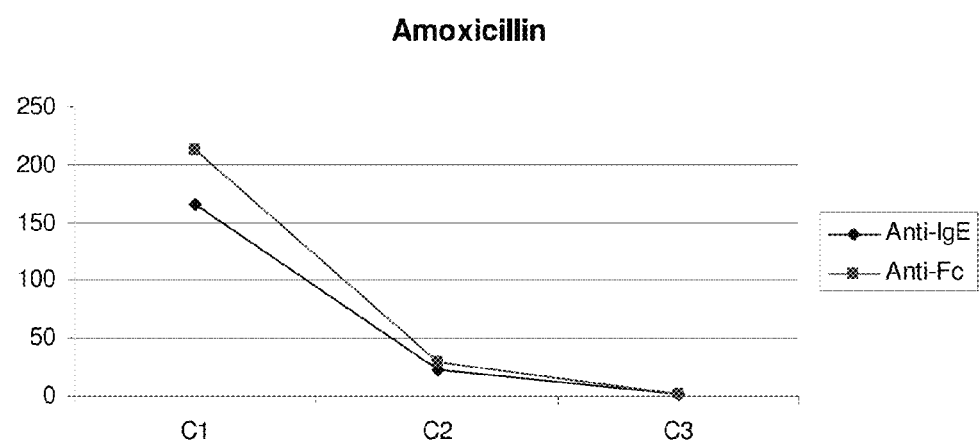
FIG. 11D shows that MFI Acivation Index using anti-FcεRI-AF647, as the basophil activation marker, was similar than the MFI Activation Index yielded by anti-IgE-AF647 in an Amoxicillin allergic patient.

In an Amoxicillin allergic patient it could be shown that MFI Acivation so Index using anti-$F_c\epsilon R1$-AF647 as the basophil activation marker was similar than the MFI Activation Index yielded by anti-IgE-AF647 (FIG. 11D) indicating a strong activation with 1 mg/ml (C1) and intermediate one with 0.2 mg/ml (C2) of Amoxicillin. 0.04 mg/ml of Amoxicillin (C3) was negative in both cases and gave approximately the same low Activation Indices as the negative control (Stimulation Buffer only; not shown).

The benefit of using anti-$F_c\epsilon RI$ is the independence from IgE molecules which must be present in the patient blood samples and/or bound on the patients' basophils when using the anti-IgE protocols. The $F_c\epsilon RI$ is constitutively expressed on the outer membrane of basophilic cells and, therefore, a more direct, stable and robust marker than IgE. This observation is also supported by the fact that approximately 10 to 15% of blood donors do not react with a positive stimulation control consisting of an anti-IgE antibody, whereas this false negative rate is far below 5% when a positive stimulation control consisting of an anti-$F_c\epsilon RI$ antibody is used.

is The following illustrative example shows the generation of positivity thresholds (cutoffs) by Receiver Operator Characteristic (ROC) curves for an important group of drug allergens, the NSAIDs.

Example 8

ROC Curves for NSAIDs Allergens 15 patients with severe allergic hypersensitivity reactions (urticaria, angiodema, anaphylactic shock) to NSAIDs (Aspirin, Diclofenac, Naproxen, Ibuprofen, Propyphenazone, Paracetamol and Metamizol) and a positive in vivo challenge test with Aspirin were compared with 13 healthy controls who all tolerated a high dose of Aspirin (500 mg or 1 g) in the in vivo challenge test.

Figure 12A:
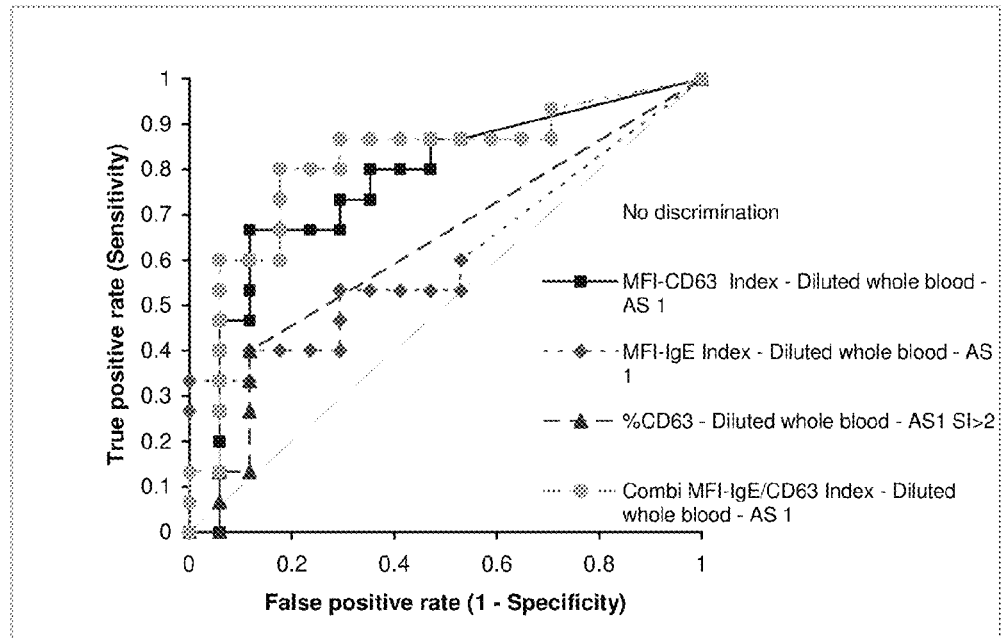
FIG. 12A shows the ROC curves for Aspirin (1 mg/ml) using the data from percentage of CD63 expression. Activation Index (AI) of MFI-IgE, Activation Index (AI) of MFI-CD63 and the combined Activation Index of MFI-IgE+MFI-CD63 were compared.
Figure 12B:
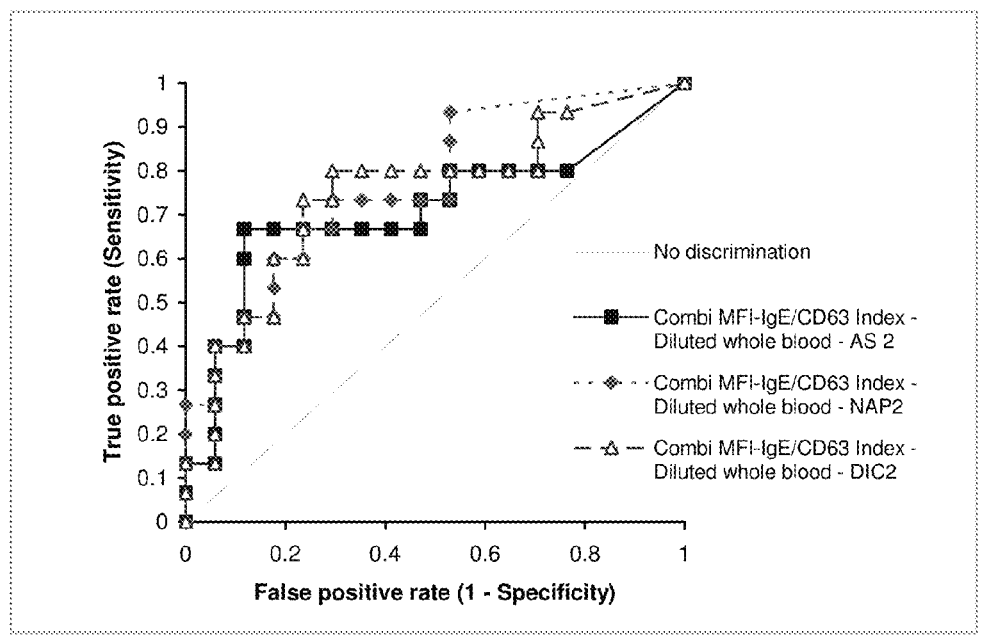
FIG. 12B shows a second comparative example of the ROC curves for Aspirin (0.2 mg/ml), Diclofenac (0.06 mg/ml) and Naproxen (0.2 mg/ml) using the data from the combined Activation Index of MFI-IgE/CD63.

Blood was drawn into EDTA venipuncture tubes and all blood samples were analyzed according to Protocol 1 and stimulated with Stimulation Buffer (negative control), anti-FcεRI mAb (positive control), 1 and 0.2 mg/ml (final dilution) of Lys-Aspirin, 1 and 0.2 mg/ml (final dilution) of Naproxen, and 0.31 and 0.06 mg/ml (final dilution) of Diclofenac, respectively. Individual results are expressed in percentage of CD63 expression, Activation Index (AI) of MFI-IgE and Activation Index (AI) of MFI-CD63. In order to find the optimum cutoff point (positivity threshold) the results of the controls were compared with those of the patients using Receiver Operator Characteristics (ROC) curves. As illustrative examples the ROC curves for Aspirin (1 mg/ml) using the data from percentage of CD63 expression, Activation Index (AI) of MFI-IgE, Activation Index (AI) of MFI-CD63 and combined Activation Index of MFI-IgE+MFI-CD63 are compared and shown in FIG. 12A. Another comparative example of the ROC curves for Aspirin (0.2 mg/ml), Diclofenac (0.06 mg/ml) and Naproxen (0.2 mg/ml) using the data from the combined Activation Index of MFI-IgE/CD63 is shown in FIG. 12B.

The cutoff point which defines the best possible sensitivity matching the best possible specificity is usually chosen at the bending of the ROC curve. The optimum cutoff (C.O.) ranges and the resulting sensitivity (SE) and specificity (SP) data for two concentrations each of Aspirin (ASA), Naproxen (NAP) and Diclofenac (DIC) are shown in Table 3. The higher concentrations of Naproxen and Diclofenac are unspecifically stimulating blood basophils and give therefore, higher Index values for patients and controls subsequently leading to markedly increased cutoff values (positivity thresholds). Specificity and sensitivity is lower and, therefore the higher concentrations of Naproxen allergen (1 mg/ml) and Diclofenac allergen (0.31 mg/ml) should not be tested or should only be used with caution. The use of the MFI-IgE, MFI-CD63 and, particularly, the combined MFI-IgE/CD63 Activation Index values leads to a dramatically higher sensitivity as compared to the percentage of CD63 expression.

Similar data were also obtained for beta-lactam antibiotics such as Penicillin G, PPL, MDM, Amoxicillin, Ampicillin and Cetriaxone. It was, therefore, concluded to choose an Activation Indices (AI) of 6 to 35, preferably below 15, as the cutoff value (positivity threshold) for all subsequent examples with drug allergens.

The following four illustrative and comparative examples show the benefits of using the MFI-IgE Index or the MFI-CD63 Index or, preferably, the Combined Activation Index in maximizing the clinical sensitivity in drug allergic patients over prior art methods using percentage of CD63 expression.

Example 9

Comparative Results for Beta-Lactam Antibiotics (Amoxicillin)

Figure 13:
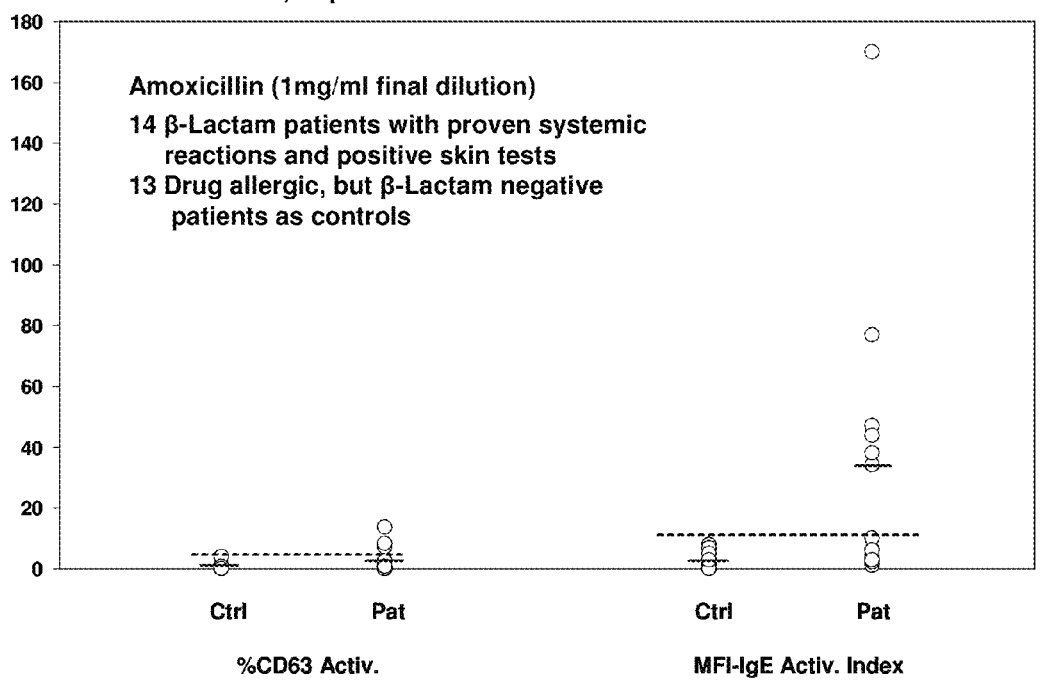
FIG. 13 shows results of Example 9 (comparative results for beta-lactam antibiotics (Amoxicillin)).

14 β-Lactam allergic patients with proven systemic reactions and positive skin tests and 13 drug allergic, but β-Lactam negative, patients as controls were tested with three concentrations each of 3 different allergens (1, 0.2 and 0.04 mg/ml of Amoxicillin, Penicillin G and Ceftriaxone) using Protocol 1 with diluted whole EDTA blood and analyzed by percentage of CD63 expression (cutoff: 5% CD63 activation, Stimulation Index≥2) and the MFI-IgE Activation index (cutoff: AI≥7), respectively. One illustrative set of results for the Amoxicillin allergen (1 mg/ml) is shown in FIG. 13. The dotted lines indicate the corresponding cutoff (positivity) thresholds. All data are summarized in Table 4. A correctly positive (SE; sensitivity) and a falsely positive (SP; specificity) result is reported when at least one result of the three different allergen concentrations was read above the corresponding cutoff thresholds. "Comb." means that all results of any concentration of the three different allergens were combined.

The use of the MFI-IgE Activation Index values leads to a significantly higher sensitivity as compared to the percentage of CD63 expression.

Example 10

Comparative Results for NSAIDs (Ibuprofen)

Figure 14:
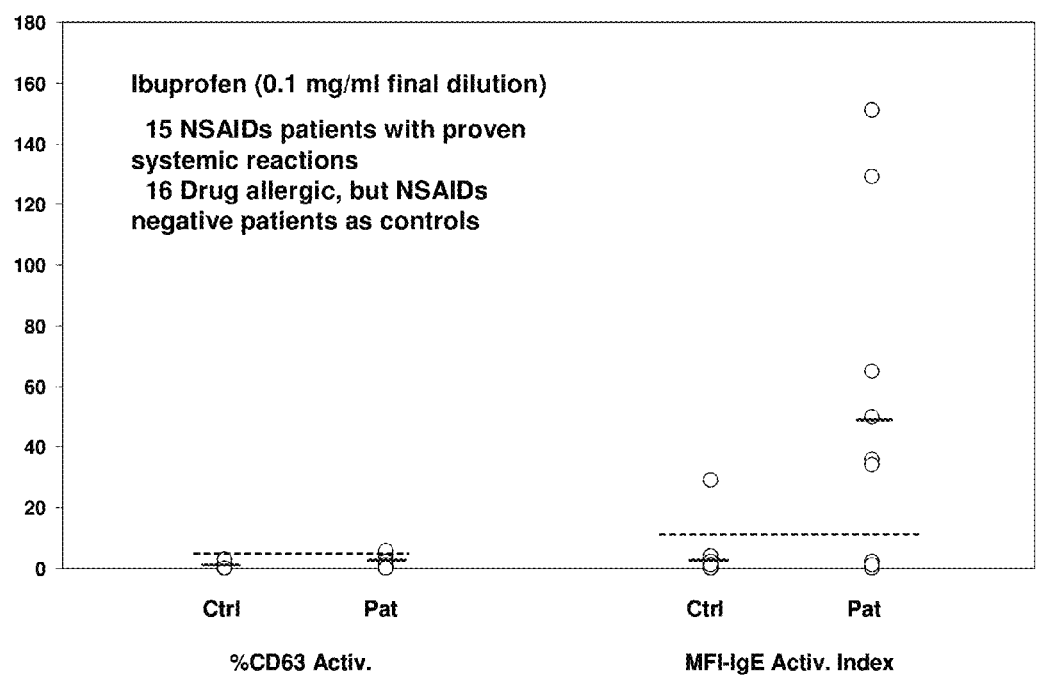
FIG. 14 shows results of Example 10 (comparative results for NSAIDs (Ibuprofen)).

15 NSAIDs allergic patients with proven systemic reactions and 16 allergic, but NSAIDs negative, patients as controls were tested with three concentrations each of 3 different allergens (1, 0.2 and 0.04 mg/ml of Lys-Aspirin and 0.1, 0.02 and 0.004 mg/ml of Ibuprofen and Ketoprofen) using Protocol 1 with diluted whole EDTA blood and analyzed by percentage of CD63 expression (cutoff: 5% CD63 activation, Stimulation Index≥2) and the MFI-IgE Activation Index (cutoff: AI≥10), respectively. One illustrative set of results for the Ibuprofen allergen (0.1 mg/ml) is shown in FIG. 14.

The dotted lines indicate the corresponding cutoff (positivity) thresholds. All data are summarized in Table 5. A correctly positive (SE; sensitivity) and a falsely positive (SP; specificity) result is reported when at least one result of the three different allergen concentrations was read above the corresponding cutoff thresholds. "Comb." means that all results of any concentration of the three different allergens were combined.

The use of the MFI-IgE Activation Index values leads to a dramatically higher sensitivity as compared to the percentage of CD63 expression.

Example 11

Comparative Results for NSAIDs (Aspirin)

Figure 15:
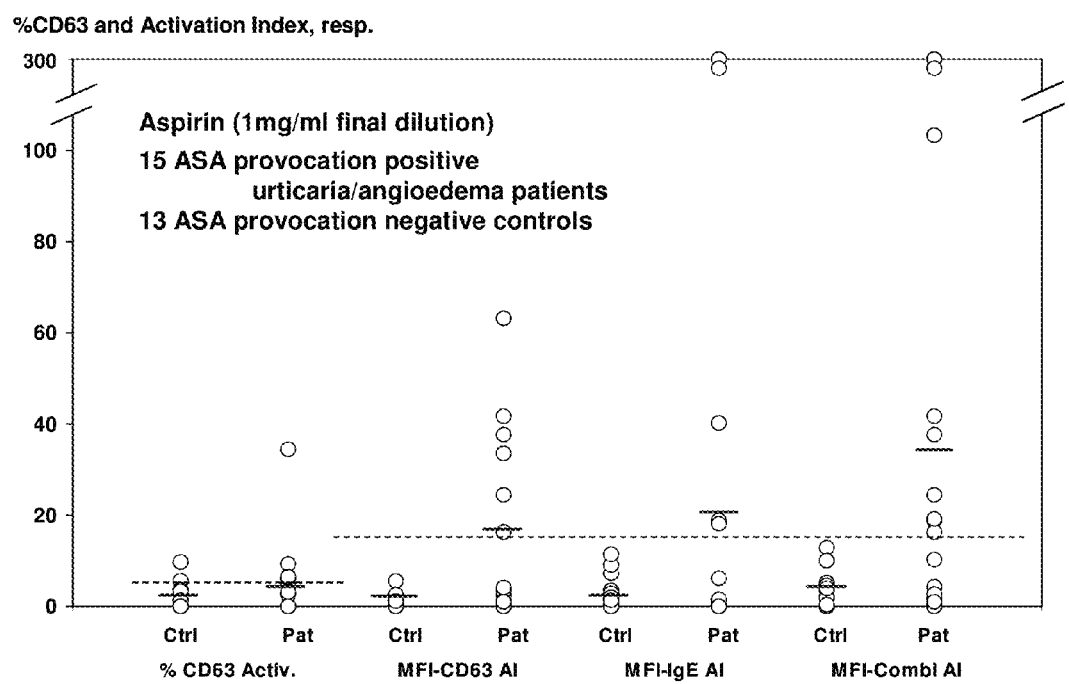
FIG. 15 shows results of Example 11 (comparative results for NSAIDs (Aspirin)).

15 patients with severe allergic hypersensitivity reactions (urticaria, angiodema, anaphylactic shock) to NSAIDs (Aspirin, Diclofenac, Naproxen, Ibuprofen, Propyphenazone, Paracetamol and Metamizol) and a positive in vivo challenge test with Aspirin and 13 healthy controls who all tolerated a high dose of Aspirin (500 mg or 1 g) in the in vivo challenge test, respectively, were tested with Lys-Aspirin (ASA; 1 and 0.2 mg/ml) Naproxen (NAP; 0.2 mg/ml) and Diclofenac (DIC; 0.06 mg/ml) using Protocol 1 with EDTA blood and analyzed by percentage of CD63 expression (cutoff for all allergens: 5% CD63 activation, Stimulation Index ≥2), the MFI-IgE Index (cutoff for Aspirin: AI≥12; cutoff for Naproxen and Diclofenac: AI≥25), the MFI-CD63 Index (cutoff for all allergens: AI≥6), and the combined MFI-IgE/CD63 Index (cutoff for Aspirin: AI≥15; cutoff for Naproxen and Diclofenac: AI≥35), respectively. One illustrative set of results for the Aspirin allergen (1 mg/ml) is shown in FIG. 15. The dotted lines indicate the corresponding cutoff (positivity) thresholds. The bold bars indicate the mean values. All data are summarized in Table 6. A correctly positive (SE; sensitivity) and a falsely positive (SP; specificity) result is reported when at least one result of the two different allergen concentrations was read above the corresponding cutoff thresholds. "Comb." means that all results of any concentration of the three different allergens were combined. The use of the MFI-IgE or MFI-CD63 Activation Index values leads to a significantly higher sensitivity as compared to the percentage of CD63 expression. When both Activation Indices are combined to the MFI-IgE/CD63 Activation Index, a clinical sensitivity of 80% or higher can be reached which is far above any reported sensitivities for NSAIDs allergic patients using prior art methods. Interestingly, this sensitivity can be reached by just using one single allergen such as Aspirin (see Table 6). Usually a combination of several allergens of one specific allergen class, such as NSAIDs, must be used to get a sufficiently high sensitivity, however as a consequence often leading to lower specificities.

Example 12

Comparative Results for Neuromuscular Blocking Reagents (NMBs)

Figure 16:
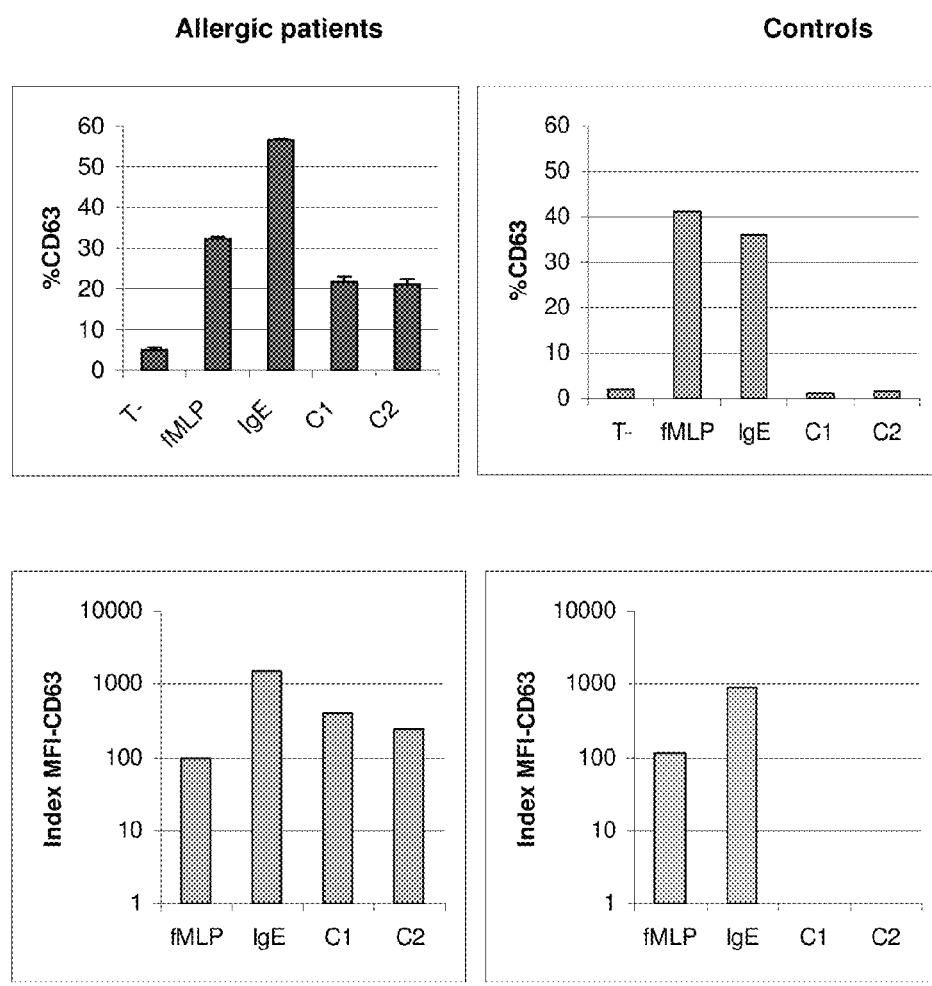
FIG. 16 shows results of Example 12 (comparative results for neuromuscular blocking reagents (NMBs)). The percentages of CD63 expression vs. combined MFI-IgE/CD63 Activation Index in NMB allergic patients are shown (allergic patients in the left panels; controls in the right panels).

10 patients having experienced an anaphylactic shock during a previous anaesthesia and presenting positive skin tests and 7 controls with no clinical history of an allergic reaction to NMBs and negative skin tests, respectively, were tested with two concentrations of a NMB mix containing Suxamethonium (100 and 20 µg/ml final dilution), Atracurium (5 and 1 µg/ml), Cis-atracurium (10 and 2 µg/ml), Vecuronium (100 and 20 µg/ml), Pancuronium (100 and 20 µg/ml), Rocuronium (50 and 10 µg/ml) and Mivacurium (1 and 0.02 µg/ml) using Protocol 1 with diluted EDTA blood and analyzed by percentage of CD63 expression (cutoff: 5% CD63 activation; Stimulation Index≥2) and the combined MFI-IgE/CD63 Activation Index (cutoff: AI≥15), respectively. The averaged data for patients and controls are presented in FIG. 16. Single patient and control results are summarized in Table 7. Using percentage of CD63 expression as the evaluation criterion two patients give a negative response, whereas the sensitivity for the combined MFI-IgE/CD63 Activation Index is 100%. The specificity for both activation parameters is perfect. Therefore, the use of the combined MFI-IgE/CD63 Activation Index values again leads to a higher sensitivity as compared to the percentage of CD63 expression. As a second control group, 18 healthy blood donors have been tested with the same conditions yielding in each case a CD63 expression below 5% and a MFI-CD63 Activation Index below 10, again indicating the high specificity of 100% for both activation markers.

The following illustrative example shows the benefit of the invented method(s) over prior art methods in solving three unclear and/or complicated patient cases.

Example 13

Real-Life Patient Cases (Table 8)

Here we describe shortly three patients (Patient 3, 6, 9) with a clear clinical history (all presenting an anaphylactic shock of grade III or IV) of NMB, β-Lactam antibiotics and NSAIDs allergy, respectively. All tested methods were clearly positive confirming the clinical history: Percentage of CD63 expression, combined MFI-IgE/CD63 Activation Index and, when tested, specific IgEs (spigE) and skin tests (prick or intradermal=IDR), whereas three control subjects (Patient 1, 4, 7) gave a negative test results for any method tested, except Patient 1 for spIgEs. Three complicated patients (Patient 2, 5, 8) with a suspected, but not clear clincal history were only positive with the combined MFI-IgE/CD63 Index, but not with % CD63 expression, confirming the suspected clincal history. Positivity thresholds (cutoffs) were chosen at 5% plus SI≥2 for percentage of CD63 expression, AI≥5 for the MFI-IgE/CD63 Activation Index, and ≥0.35 kU/l for the specific IgE results, respectively. Positive results are indicated by the shaded boxes. The allergen concentrations (c1, c2) were the same as used for β-Lactam Antibiotics, NSAIDs and NMBs in the previous examples (c3 is a 1 in 5 dilution of c2). NC is the negative control value (Stimulation Buffer only). The MFI-IgE and MFI-CD63 data are used for the calculation of the combined MFI-IgE/CD63 Activation Index (AI) by the formula described in this invention.

Patient (f, 42): Hairdresser having experienced a perianesthetic shock on the occasion of a tooth extraction and, therefore, suspected to be allergic to muscle relaxants (NMBs). It could be shown that the shock was not caused by NMBs.

Patient 2 (m, 59): In December 2006, the patient experienced an anaphylactic shock, grade III, during a surgery after intravenous application of the muscle relaxant, atracurium. From the clinical history, the skin tests and the measurements of spIgEs, but not from CD63 expression, it was a clear NMB allergy. The combined MFI-IgE/CD63 Activation Index confirmed the clinical history.

Patient 3 (f, 18): The patient experienced a severe, life-threatening anaphylactic shock, grade IV, during a surgery after intravenous application of the muscle relaxant, suxamethonium. This clinical history could be confirmed by all methods.

Patient 4 (f, 46): The patient experienced a perianaesthetic shock during a surgery induced by the muscle relaxant, atracurium. The suspected hypersensitivity reaction to Amoxicillin which was also given before the surgery to this patient could be excluded by the negative result of all methods tested.

Patient 5 (f, 42): A patient with a systemic reaction after intake of Amoxicillin was positive with skin test, but could not be tested with spIgEs. CD63 expression was negative, however the positive result with the combined MFI-IgEICD63 Activation Index confirmed the clinical history.

Patient 6 (f, 37): The patient experienced a severe allergic reaction a few minutes after intake of (β-Lactam antibiotics. This clinical history could be confirmed by all methods tested.

Patient 7 (f, 43): The patient experienced a large local, but not systemic, reaction after a wasp sting. Since the patient also reported never getting any problem after intake of NSAIDS such as aspirin, she was tested as negative control for NSAIDs. Both CD63 expression and the combined MFI-IgE/CD63 Activation Index gave clearly negative results, indicating the excellent specificity of the basophil stimualtion methods. Due to ethical reasons skin tests for NSAIDs were not run, since there was no objection from the clinical history to do so. SpIgE tests are not available for NSAIDs.

Patient 8 (m, 16): A patient with psoriasis experienced an acute relapse after intake of NSAIDs. CD63 expression was negative and skin test were not applicable due to the strong psoriasis. With the invented method showing positive results with the combined MFI-IgE/CD63 Activation Index for both Aspirin (ASA) and Ibuprofen (IBU) the acute relapse could be clearly related to the intake of and, therefore, a hypersensitivity reaction to the ingested NSAIDs.

Patient 9 (m, 35): Two hours after intake of Ibuprofen the patient reported respiratory difficulties, developed a generalized urticaria and was then admitted to the intensive care unit. Both CD63 expression and the combined MFI-IgE/CD63 Activation Index showed a clearcut reaction with aspirin (ASA), Ibuprofen (IBU) and Diclofenac (DIC) confirming the clinical history. Skin tests were not made and spigE tests are not available for NSAIDs, respectively.

Summing up, the use of said invention leads to a significant increase of the clinical sensitivity of flow cytometry applied to drug allergy and drug hypersensitivity diagnosis, such a high sensitivity being mandatory for the routine use of this method, in replacement of in vivo tests, such as skin tests and in vivo provocation tests, which are time consuming and may be dangerous for the patient with the additional aim of decreasing the costs of such difficult explorations.

The invention claimed is:
1. A method for the determination of basophil activation induced by a test substance comprising
  contacting the basophils with a plurality of antibodies comprising anti-CD63 antibody, anti-IgE antibody and anti-CCR3 antibody, each of which is independently labeled with a fluorophore, wherein said anti-CCR3 antibody acts as a selection marker and said anti-CD63 antibody and said anti-IgE antibody each independently act as an activation marker;

measuring, via a flow cytometer, a change in the mean or median fluorescence intensity (MFI) of the IgE antibodies bound to the $F_c\epsilon RI$ receptor on the cell surface of basophils (MFI-IgE) and the anti-CD63 antibodies bound to the CD63 antigen exposed on the cell surface of basophils after activation (MFI-CD63); and correlating the changes of the mean fluorescence intensities of said activation markers in the presence and absence of said test substance to obtain an Activation Index which is either the sum or the product of the activation index for parameter A (y(A)) and parameter B (y(B)), wherein A is the mean or median fluorescence intensity (MFI) of CD63 (MFI-CD63) and B is the MFI of IgE (MFI-IgE) and y for each parameter is calculated in terms of $$y = \frac{a-d}{\left(1+\left(\frac{x}{c}\right)^b\right)} + d$$

wherein
i) a is the minimum value of the function curve,
ii) b is the slope of the curve,
iii) c is the turning point of the curve,
iv) d is the maximum asymptotic value of the curve, and
v) x is
1 minus the ratio between (A) of the negative control and (A) of the test substance, or
1 minus the ratio between (A) of the negative control and (A) of the positive control, or
1 minus the ratio between (B) of the negative control and (B) of the test substance, or
1 minus the ratio between (B) of the positive control and (B) of the negative control.

2. A method according to claim 1, wherein the test substance is a mitogen, an antigen, an allergen, a protein or peptide, a protein or peptide allergen, a group or mixture of protein and/or peptide allergens, a non-proteinaceous allergen, a low molecular weight allergen, a low molecular weight drug substance or a hapten.

3. A method according to claim 2, wherein the antigen or allergen has a molecular weight below 1000 Da.

4. A method according to claim 2, wherein the allergen is a non-proteinaceous allergen, a paucivalent allergen or a true hapten.

5. A method according to claim 2, wherein the allergen is a low molecular weight drug substance.

6. A method according to claim 5, wherein the drug substance is an antibiotic, an antiseptic, a fungicide, an antiviral agent, an anti-malarial agent, an analgesic, a COX-2 inhibitor, a non-steroidal anti-inflammatory drug, a neuromuscular blocking agent, a hypnotic or a local anesthetic, a tranquilizer, an opioid, a radio-contrast media, a proton inhibitor, an anti-convulsant or a neuroleptic, an antipsychotic agent, an anti-depressant, a dopamine, an anti-histamine, a corticosteroid, a glucocorticoid, a chemotherapeutic or an immunosuppressive agent; a diuretic agent; an anticoagulant; a vasoconstrictor or a vasodilatator; a cardiac drug, an ACE inhibitor, an alpha-receptor blocker, a beta-receptor blocker, a calcium antagonist or a anti-hypertonic agent; an (anti-)ulcer drug; an (anti-)thyroid drug; estrogen; a heparin or a derivative thereof; insulin; a streptokinase or a urokinase; or a drug which causes adverse drug reactions or a drug which causes hypersensitivities.

7. A method according to claim 2, wherein the allergen is a colloid, plasma expander or auxiliary agent.

8. A method according to claim 7, wherein the colloid, plasma expander or auxiliary agent is selected from the group consisting of albumine, dextrane, gelatine, hetastarch, pentastarch, sinistrin, polydocanol 600 (ethoxysclerol), lactose, carboxymethylcellulose, hydroxypropylcellulose, protamine and aprotinine.

9. A method according to claim 2, wherein the allergen is a food additive.

10. A method according to claim 9, wherein the food additive is selected from the group consisting of food preservatives, food colorants, food finishers, anti-oxidants, and emulsifiers.

11. A method according to claim 2, wherein the allergen is an occupational, environmental or pollutant agent.

12. A method according to claim 11, wherein the occupational, environmental or pollutant agent is selected from the group consisting of isocyanates, isothiazolinones, formaldehyde, ethylene oxide, phthalic anhydride, chloramine T, DMSO, latex, and enzymes used in the baking, food processing and washing industry.

13. A method according to claim 2, wherein the test substance is a single allergen or a mixture of any combination of allergens.

14. A method according to claim 1, wherein the test substance is a protein or peptide allergen or a mixture of protein allergens and/or peptide allergens.

15. An in vitro allergy test comprising the steps of
(a) incubating either
   i. an anti-coagulated and diluted human or animal whole blood sample, or
   ii. an anti-coagulated and subsequently purified human or animal blood sample with a test substance for 5 to 120 minutes to activate the basophils in said sample,
(b) stopping said activation by
   i) adding a stop solution containing EDTA to said sample, and/or
   ii) putting said sample immediately at 0 to 5° C.,
(c) adding to said sample a plurality of antibodies comprising
   i) anti-CCR3 as selection marker, and,
   ii.) anti-CD63 and anti-IgE as activation markers, and incubating said sample mixture for 5 to 45 minutes, at 2 to 8° C.,
(d) optionally lysing remaining erythrocytes in said sample mixture and analysing it on a flow cytometer,
(e) measuring the basophil activation, as expressed as a change in the mean or median fluorescence intensity (MFI) of the IgE antibodies bound to $F_c\epsilon RI$ receptor on the cell surface of basophils (MFI-IgE) and the CD63 antigen exposed on the cell surface of basophils after activation (MFI-CD63), in said sample mixture induced by said test substance,
(f) calculating the basophil Activation Index which is either the sum or the product of the activation index for parameter A (y(A)) and parameter B (y(B)),
   wherein A is the mean or median fluorescence intensity (MFI) of CD63 (MFI-CD63) and B is the MFI of IgE (MFI-IgE) and y for each parameter is calculated in terms of $$y = \frac{a-d}{\left(1+\left(\frac{x}{c}\right)^b\right)} + d$$

wherein
i) a is the minimum value of the function curve,
ii) b is the slope of the curve,
iii) c is the turning point of the curve,
iv) d is the maximum asymptotic value of the curve, and
v) x is
- 1 minus the ratio between (A) of the negative control and (A) of the test substance, or
- 1 minus the ratio between (A) of the negative control and (A) of the positive control, or
- 1 minus the ratio between (B) of the negative control and (B) of the test substance, or
- 1 minus the ratio between (B) of the positive control and (B) of the negative control.

16. The in vitro allergy test according to claim 15, wherein the concentration of the test substance in the sample is between 0.1 ng/ml to 10 mg/ml.

17. The in vitro allergy test according to claim 15, wherein the test substance is a mitogen, an antigen, an allergen, a protein or peptide, a protein or peptide allergen, a group or mixture of protein and/or peptide allergens, a non-proteinaceous allergen, a low molecular weight allergen, a low molecular weight drug substance or a hapten.

18. The in vitro allergy test according to claim 15, wherein the whole blood sample or purified blood sample comprises EDTA as anticoagulant.

19. The in vitro allergy test according to claim 15, wherein the whole blood sample or purified blood sample has a volume between 10 and 200 µl.

20. The in vitro allergy test according to claim 15, wherein before step a) interleukin-3 is added to the whole blood sample or purified blood sample.

21. The in vitro allergy test according to claim 20, wherein said interleukine-3 is added in an amount resulting in a concentration of 0.2 to 20 ng/ml.

22. The in vitro allergy test according to claim 15, wherein steps a) and c) are carried out simultaneously for 5 to 120 minutes.

23. The in vitro allergy test according to claim 15, wherein lysis step d) is omitted and said sample mixture is directly measured on a flow cytometer.

24. An ex vivo method for measuring allergic and drug hypersensitivity or the response to a hyposensitization therapy of said allergic or drug hypersensitivity in a hypersensitive patient, comprising contacting said patient's basophils with a plurality of antibodies comprising anti-CD63 antibody, anti-IgE antibody and anti-CCR3 antibody, each of which is independently labeled with a flourophore, wherein said anti-CCR3 antibody acts as a selection marker and said anti-CD63 antibody and said anti-IgE antibody act as an activation markers;

determining a change in the mean or median fluorescence intensities (MFI) of the the IgE antibodies bound to the $F_c\epsilon RI$ receptor (MFI-IgE) and the CD63 antigen exposed on the cell surface of basophils after their activation (MFI-CD63) in the presence of a test substance, a negative control sample, and a positive control sample; and correlating the changes of the mean fluorescence intensities of said activation markers to obtain an Activation Index;

wherein the presence or absence of an allergic or drug hypersensitivity or the success or failure of a hyposensitization therapy is determined by comparing the Activation Index values, wherein the Activation Index is either the sum or the product of the activation index for parameter A (y(A)) and parameter B (y(B)), wherein A is the mean or median fluorescence intensity (MFI) of CD63 (MFI-CD63) and B is the MFI of IgE (MFI-IgE) and y for each parameter is calculated in terms of $$y = \frac{a-d}{\left(1+\left(\frac{x}{c}\right)^b\right)} + d$$

wherein
i) a is the minimum value of the function curve,
ii) b is the slope of the curve,
iii) c is the turning point of the curve,
iv) d is the maximum asymptotic value of the curve, and
v) x is
- 1 minus the ratio between (A) of the negative control and (A) of the test substance, or
- 1 minus the ratio between (A) of the negative control and (A) of the positive control, or
- 1 minus the ratio between (B) of the negative control and (B) of the test substance, or
- 1 minus the ratio between (B) of the positive control and (B) of the negative control.

25. A method according to claim 1, wherein the determination of said basophil activation is indicative of allergy or hypersensitivity to said test substance.

26. A method according to claim 1, wherein said determination of basophil activation induced by a test substance monitors the response to a hyposensitization therapy.

27. A method according to claim 1, wherein the Activation Index is a dimensionless, arbitrary value ranging between 0 and 500.

28. A method according to claim 1, wherein a positive test correlates with an Activation Index of greater than 6.

* * * * *